United States Patent
Tereba et al.

(10) Patent No.: US 6,673,631 B1
(45) Date of Patent: *Jan. 6, 2004

(54) SIMULTANEOUS ISOLATION AND QUANTITATION OF DNA

(75) Inventors: Allan M. Tereba, Fitchburg, WI (US); Rex M. Bitner, Cedarburg, WI (US); Susan C. Koller, Verona, WI (US); Craig E. Smith, Oregon, WI (US); Daniel D. Kephart, Cottage Grove, WI (US); Steven J. Ekenberg, Mount Horeo, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/377,986

(22) Filed: Aug. 20, 1999

Related U.S. Application Data

(63) Continuation-in-part of application No. 08/785,097, filed on Jan. 21, 1997, now Pat. No. 6,027,945.

(51) Int. Cl.[7] .......................... C12Q 1/68; G01N 33/552; G01N 33/553; C12P 19/34; C07H 21/00

(52) U.S. Cl. ........................ 436/526; 436/527; 435/6; 435/91.1; 423/335; 536/25.42

(58) Field of Search .................. 435/6, 91.1, 287.2; 436/501, 526, 527; 423/335; 536/25.42

(56) References Cited

U.S. PATENT DOCUMENTS

| | | | |
|---|---|---|---|
| 4,233,169 A | 11/1980 | Beall et al. | 252/62.59 |
| 4,297,337 A | 10/1981 | Mansfield et al. | 424/1 |
| 4,395,271 A | 7/1983 | Beall et al. | 65/31 |
| 4,672,040 A | 6/1987 | Josephson | 436/526 |
| 4,683,202 A | 7/1987 | Mullis | 435/91 |
| 4,695,393 A | 9/1987 | Whitehead et al. | 252/62.54 |
| 4,699,717 A | 10/1987 | Riesner et al. | 210/635 |
| 4,767,670 A | 8/1988 | Cox et al. | 428/403 |
| 5,057,426 A | 10/1991 | Henco et al. | 435/270 |
| 5,075,430 A | 12/1991 | Little | 536/27 |
| 5,076,950 A | 12/1991 | Ullman et al. | 252/62.51 |
| 5,155,018 A | 10/1992 | Gillespie et al. | 435/91 |
| 5,234,809 A | 8/1993 | Boom et al. | 435/91 |
| 5,316,680 A | 5/1994 | Frechet et al. | 210/635 |
| 5,346,994 A | 9/1994 | Chomczynski | 530/419 |
| 5,389,449 A | 2/1995 | Afeyam et al. | 428/523 |
| 5,395,498 A | 3/1995 | Gombinsky et al. | 204/182.8 |
| 5,482,834 A | 1/1996 | Gillespie | 435/6 |
| 5,523,231 A | 6/1996 | Reeve | 435/270 |
| 5,582,988 A | 12/1996 | Backus et al. | 435/6 |
| 5,610,274 A | 3/1997 | Wong | 530/334 |
| 5,652,348 A | 7/1997 | Burton et al. | 536/20 |
| 5,658,548 A | 8/1997 | Padhye et al. | 423/335 |
| 5,660,984 A | 8/1997 | Davis et al. | 435/6 |
| 5,681,946 A | 10/1997 | Reeve | 536/25.4 |
| 5,728,822 A | 3/1998 | Macfarlane | 536/25.41 |
| 5,734,020 A | 3/1998 | Wong | 530/350 |
| 5,747,663 A | 5/1998 | Colpan et al. | 536/24.5 |
| 5,783,686 A | 7/1998 | Gonzalez | 536/24.5 |
| 5,945,525 A * | 8/1999 | Uematsu et al. | 536/25.42 |
| 5,990,301 A | 11/1999 | Colpan et al. | 536/24.5 |
| 6,027,945 A | 2/2000 | Smith et al. | 536/526 |
| 6,410,725 B1 * | 6/2002 | Scholl et al. | |

FOREIGN PATENT DOCUMENTS

| | | |
|---|---|---|
| CA | 2223821 | 6/1996 |
| DE | 4307262 A1 | 9/1994 |
| JP | 09327290 | 12/1997 |
| JP | 09327291 | 12/1997 |
| JP | 10-316696 | 12/1998 |
| WO | WO 95/06652 | 3/1995 |
| WO | WO 97/29825 | 8/1997 |
| WO | WO 98/31461 | 7/1998 |
| WO | WO 98/31840 | 7/1998 |

OTHER PUBLICATIONS

Matsubara et al, Wizard Minipreps DNA Purfication Systems, Dec. 1994, Promega, pp. 1–4.*

Matsubara et al. "Dried blood spot on filter paper as a source of mRNA", Nucleic Acids Research, Vol 20, No. 8, p 1998, 1992.*

Floyd et al., "Mixed–Mode Hydrophobic Ion Exchange for the Separation of Oligonucleotides and DNA Fragments Using HPLC", *Analytical Biochemistry* (1986) 154:570–577.

Gjerde et al., Ion Chromatography, Ch. 3, Dr. Alfred Hothig Verlag Heidelberg (1987) 2nd Ed.

(List continued on next page.)

*Primary Examiner*—Karen Lacourciere
(74) *Attorney, Agent, or Firm*—Michael Best & Friedrich LLP; Grady J. Frenchik; Jill A. Fahrlander

(57) ABSTRACT

The present invention provides methods for isolating a defined quantity of DNA target material from other substances in a medium. The method may be carried out using a known quantity of a silica-containing solid support, such as silica magnetic particles, having a definable capacity for reversibly binding DNA target material, and DNA target material in excess of the binding capacity of the particles. The methods of the present invention involve forming a complex of the silica magnetic particles and the DNA target material in a mixture of the medium and particles, and separating the complex from the mixture using external magnetic force. The DNA target material may then be eluted from the complex. The quantity of DNA target material eluted may be determined based on a calibration model. The methods of the present invention permit isolation of DNA target material which is within a known quantity range. The methods of the invention eliminate the step of quantitating purified biological samples prior to further processing, such as amplification, Short Tandem Repeat (STR) analysis, and DNA sequencing. Samples of the DNA target materials may be obtained from liquid or solid media, such as liquid blood or paper.

29 Claims, 3 Drawing Sheets

OTHER PUBLICATIONS

Goldsborough et al., "High Purity Plasmid DNA from Anion Exchange Chromatography", *Focus* (1998) vol. 20 No. 3.

Jost et al., "Application of a Weakly Basic Dimethylamino–Modified Silica Ion Exchanger to the Separation of oligonucleotides", *J. Chromatog.* 185 (1979) 403–412.

Kirk–Othmer, Encyclopedia of Chemical Technology, (1997)Vol. 21, 4th ed., 1997, pp. 1021–1022.

Maa et al., "Rapid high–performance liquid chromatography of nucleic acids with polystyrene–based micropellicular anion exchangers", *J. Chromatog.* (1990) 508:61–73.

Macherey–Nagel, Macherey–Nagel homepage on the Internet on Jun. 12, 1998, at //www.machrey–nagel.com.

McLaughlin, L., "Mixed–Mode Chromatography of Nucleic Acids", *Chem Rev* (1989) 89:309–319.

Northrop et al., "Preparation and Evaluation of a Bimodal Size–Exclusion Chromatography Column Containing a Mixture of Two Silicas of Different Pore Diameter", *Anal. Chem.* (1991) 63:1350–1354.

Promega, Technical Bulletin No. 202 Wizard ® Plus Series 9600 ™ DNA Purification System, (Promega Corp.) (9/98).

Promega, Technical Bulletin No. 225 Wizard ® Plus SV Minipreps DNA Purification System, (Promega Corp.) (9/99).

Promega, Technical Bulletin No. 259 Wizard ® PureFection Plasmid DNA Purification System, (Promega Corp.) (9/99).

Sambrook et al., Molecular Cloning a Laboratory Manual, 2nd ed. pp. 1.25–1.28 (1989).

Waterborg et al., "Efficient large–scale purification of restriction fragments by solute–displacement ion–exchange HPLC", *Nucleic Acids Research* (1993) vol. 21, No. 12:2913–2915.

Bischoff et al., "Chemically Synthesized Hydrophobic Anion–Exchange High–Performance Liquid Chromatography Supports Used for Oligonucleotide Resolution By Mixed Mode Chromatography", *J. Chromatog.* (1983) 270:117–126.

Bischoff et al., "Nucleic Acid Resolution By Mixed–Mode Chromatography", *J. Chromatog.* (1984) 296:329–337.

Crowother et al., "High–Performance Liquid Chromatographic Separation of Oligonucleotides and Other Nucleic Acid Constituents on Multifunctional Stationary Phases", *J. Chromatog.* (1983) 282:619–628.

Edwardson et al., "Separation and purification of oligonucleotides using a new bonded–phase packing material", *J. Chromatog.* (1991) 545:79–89.

Gibco BRL Products & Reference Guide 1997/1998, Life Technologies, "Aces 2.0+ Human DNA Quantitation System", p. 19–28.

QuantiBlot Human DNA Quantitation System, PE Applied Biosystems, Feb. 5, 1996, p. 1–5 (www.pebio.com/fo/773503/773503.html).

The validation of a 7–locus multiplex STR test for use in forensic casework, *Int J Legal Med* (1996) 109: 195–204.

Validation of highly discriminating multiplex short tandem repeat amplification systems for individual identification, *Electrophoresis* (1996) 17: 1283–1293.

Chapter 2 (DNA) and Chapter 4 (RNA) of F. Ausubel et al., eds., *Current Protocols in Molecular Biology*, Wiley–Interscience, New York (1993).

Marko et al., *Anal. Biochem.* 121, pp. 382–387 (1982).

Vogelstein et al., *Proc. Natl. Acad. Sci.* (USA) 76, pp. 615–619 (1979).

Boom et al., *J. Clin. Microbiol.* 28, pp. 495–503 (1990).

Chen et al., *Anal. Biochem*, 101, pp. 339–341 (1980).

*Kirk–Othmer Encyclopedia of Chemical Technology*, vol. 6, 4th ed., Mary Howe–Grant, ed., John Wiley & Sons, pub., 1993, pp. 773–775.

Wirth et al., *Science*, 275, pp. 44–47 (1997).

Database CAS online. AN 126:182277, Uematsu et al., 'Magnetic carriers for the separation of nucleic acids and methods of using them'. Jpn. Kokai Tokkyo Kohn, 9 pp. 21 Jan. 1997, abstract (corresponds to EP O 757 106 A2 in English).

Database CAS online. AN 126 86772, Kleiber et al., Magnetic particles and their use for isolation of biological materials'. Ger. Offen., 9 pp. Dec. 12, 1996, abstract.

* cited by examiner

US 6,673,631 B1

SIMULTANEOUS ISOLATION AND QUANTITATION OF DNA

CROSS REFERENCE TO RELATED APPLICATIONS

This application is a Continuation-In-Part of U.S. patent application Ser. No. 08/785,097 U.S. Pat. No. 6,027,945 entitled METHODS OF ISOLATING DNA TARGET MATERIALS USING SILICA MAGNETIC PARTICLES and filed Jan. 21, 1997, which application is herein fully incorporated by reference.

FIELD OF THE INVENTION

The present invention relates to methods for isolating a defined quantity of a DNA target material from other substances in a medium to produce a suitable quantity of isolated DNA target material for further processing or analysis. The present invention particularly relates to methods for isolating a defined amount of DNA target material using a silica-containing solid support capable of reversibly binding a definable quantity of the DNA target material, such as magnetically responsive particles comprising silica or a silica derivative.

BACKGROUND OF THE INVENTION

Many analysis techniques which involve the testing of a DNA target material present in a particular medium only work well when the DNA target material is isolated from other material in the medium, and quantified after isolation therefrom. Isolation of a DNA target material from other components in a forensics sample (e.g. bodily fluids collected from a crime scene, blood or buccal cells collected from suspects, etc.) is critical to ensure that the other components present in the sample do not interfere with analysis of the DNA target material. Unfortunately, forensic samples are frequently so small or so degraded that quantitation of DNA target material isolated therefrom can be time consuming and difficult. Moreover, the variance between individuals in the amount of leukocytes present in a given volume of blood further increases the variance of the quantity of DNA isolated.

With the advent of DNA typing as a tool for paternity testing and for identification of biological samples present at crime scenes has come the need to develop reliable methods for isolating and quantifying small amounts of genomic DNA. In the United States, the need to develop such systems has come from Federal Bureau of Investigation establishment of a database of analytical results from thirteen short tandem repeat ("STR") loci of human genomic DNA. These results are entered into a centralized database referred to as the Combined DNA Index System ("CODIS"). STR analysis systems are based upon the use of amplification reactions, which enable one to analyze very small amounts of DNA, even sub-nanogram amounts. However, amplification only works well when the amount of DNA to be amplified is within a defined range, and when it is substantially isolated from contaminants which can inhibit or interfere with the amplification reaction. Thus, before STR loci can be amplified and analyzed, the target DNA must be purified and quantitated to reduce the risk of observing amplification artifacts. Quantitation is important in other applications as well, such as DNA sequencing.

Procedures currently used to isolate and quantify genomic DNA for use in genetic identity typing are time consuming, and too disjointed to be amenable to automation. For example, the following procedure is typically used to isolate and quantify genomic DNA for amplification and analysis of STR loci, such as the CODIS loci. First, blood or buccal swabs are obtained from individuals using a variety of devices and volumes. Second, these samples are processed to isolate DNA of variable purity and integrity. Third, the DNA is quantitated for downstream procedures so that the appropriate amount can be used to avoid artifacts. Fourth, the DNA is amplified using reactions that include primers specific for each of the STR loci to be analyzed. Finally, the amplification products are analyzed on a gel or capillary electrophoresis system for genotype identification. For a commercial system designed for use in co-amplifying and analyzing all thirteen CODIS loci, see GenePrint® PowerPlex™ 1.1 and GenePrint® PowerPlex™ 2.1 systems (Promega Corporation, Madison, Wis.).

White blood cells are the primary source of DNA in the blood. There is considerable variability in the white blood cell content of blood, due either to variability between individuals or variability of samples from a given individual based on the health of the individual at the time the sample was obtained. A similar variability exists in buccal swab samples, compounded by variability in the type of swab used, and storage conditions of the sample before sample processing.

Both inside and outside the context of amplification of genomic DNA for DNA typing analysis, discussed above, with amplification via the polymerase chain reaction (PCR), too little template results in low band intensity or no resultant band amplification. Excess DNA template frequently results in overamplification. Overamplification is recognized by an excessive number of artifact peaks and stutter bands—defined as a minor peak directly below a major allele peak. There may also be a high incidence of background activity and "pull-up", defined as the inability to separate the different color bands in a multiplex. Reamplification of a lesser quantity of DNA may be required if excessive artifacts are present. Stutter bands are particularly pronounced when excess DNA is present and capillary electrophoresis is used for the separation of PCR amplification products. Also, as with sequencing, the generation of full length amplification products can be inhibited when too much template DNA is present. In other words, in PCR amplification, excess template DNA can lead to the presence of partially amplified fragments and low amounts of completely amplified products.

More specifically, when PCR or other amplification methods are used in forensic applications to amplify DNA, when too much DNA is amplified in a single reaction, the sample is overamplified and the signal strength of the anticipated bands tends to fall outside the desired range of the detector. Traditionally, these difficulties are minimized by quantification of DNA after its purification, which requires additional steps, time and cost. In genetic identity testing, the presence of DNA in excess of that recommended for the analysis system employed often leads to uninterpretable results; this can waste very limited samples, particularly in the case of forensic analysis.

Another DNA application which requires accurate quantitation of the nucleic acid is sequencing. Sequencing of DNA is best done on samples of target DNA which have been isolated from other material present in a medium which can interfere with the sequencing reaction. It is also necessary to quantify samples of target DNA prior to initiation of a sequencing reaction. For example, in the area of DNA sequencing, the amount of DNA template in the sequencing reaction must be within a fairly narrow range. For example, when using plasmid DNA, 150–300 ng of DNA is recommended when using automated sequencing with BigDye™ Chemistry (Perkin Elmer Biosystems). When using PCR products as sequencing templates with the same sequencing system, 40–80 ng of DNA is recommended. Too much template may result in short sequence read length, poor resolution or higher error rates. With too little template, the signal strength is too weak for optimal sequence reading.

Plasmid DNA is typically a source of DNA for sequencing reactions. There is considerable variability in plasmid DNA content within a population of bacterial cultures due to such factors as variability in plasmid copy number per cell, variability in growth media used, and concentration of cell mass.

There are a variety of methods currently used to quantitate a DNA target material in a sample. One such method is spectrophotometric determination. In this method, absorbance readings of a sample of unknown concentration are taken at the wavelength corresponding to the maximum absorbance of the DNA target material. For example, absorbance at 260 nanometers (nm) ("$A_{260}$") is used to determine the concentration of DNA in a solution, while absorbance at 280 nm ("$A_{280}$") is used to determine the concentration of protein in a solution. An absorbance reading at 260 nm of 1 corresponds to about 50 micrograms (50 $\mu$g) per milliliter ($\mu$g/ml) for double-stranded DNA, 40 $\mu$g/ml for single-stranded DNA and RNA, and about 20 $\mu$g/ml for single-stranded oligonucleotides. The ratio between the readings at 260 nm and 280 nm ("$A_{260}/A_{280}$") provides an estimate of the degree to which a given target nucleic acid has been isolated from proteins and any other materials which absorb at 280 nm. Pure nucleic acid preparations have $A_{260}/A_{280}$ values of at least about 1.8. A limitation of the spectrophotometric method is that it is not sensitive enough to be used to detect and quantitate low amounts of nucleic acid. If a nucleic acid concentration in a sample is less than about 500 nanograms per milliliter (ng/ml), or if the sample is contaminated with other substances that either absorb or quench ultraviolet irradiation, inaccurate results are obtained.

Another method for quantitating DNA after it is isolated is the use of intercalating dyes such as ethidium bromide, SyberGreen (Molecular Dynamics, Sunnyvale, Calif.) or PicoGreen (Molecular Probes, Eugene, Oreg.). Dyes are often used when there is not enough DNA to accurately measure spectrophotometrically. The amount of fluorescence of ethidum bromide, when visualized with an ultraviolet (UV) light source, is proportional to the total mass of DNA. Therefore, a standard curve of known amounts of DNA and a known amount of a sample of unknown concentration may be run into an agarose gel and the gel subsequently stained with ethidium bromide and viewed with a UV light. This type of gel is called a yield gel. The quantity of DNA in the sample can be estimated by comparing the fluorescence of the sample with the fluorescence of the standards. Similarly, this method can be performed in solution with DNA intercalating dyes. DNA levels as low as about 25 pg/ml may be detected with PicoGreen. A limitation of the yield gel method or the use of dyes to quantitate DNA in solution is that it requires a visual, spectrophotometric or fluorometric approximation of the yield by comparison to another DNA sample. The variability in results obtained using this method is high and it is also prone to error resulting from contaminating components in the DNA sample.

At least two commercial kits are available for the quantitation of low amounts of human genomic DNA after isolation. These are the ACES™ 2.0 Human DNA Quantitation Probe Plus System produced by Life Technologies, Inc. (Gaithersburg, Md.) and the Quantiblot® Human DNA Quantitation Kit produced by PE Applied Biosystems (Foster City, Calif.). These kits are typically used in laboratories performing genetic identity testing with human DNA. The Quantiblot® system is based on hybridization of a primate-specific biotinylated oligonucleotide probe to isolated DNA samples. The detection can be either colorimetric or chemiluminescent; either detection method is able to quantitate from 0.15 to 10 ng of human DNA. However, the test takes up to two hours. Furthermore, the chemiluminescent method requires X-ray film and processing capabilities, and can only be used for DNA from primates. The ACES™ System is a similar system in that it requires binding of the DNA sample to a membrane and hybridization to a human-specific DNA probe and visualization by luminescence. This system is able to quantitate from 0.04 to 40 ng of human DNA. Both of these systems, have the same limitation as that of intercalating dyes; namely, they require a visual approximation of the yield by comparison to another DNA sample.

There is a need in the art for methods capable of removing a defined amount of DNA target material from a sample containing an excess of DNA target material. These defined DNA quantities can then be subsequently used in techniques in which having excess DNA present is detrimental to obtaining interpretable results. Such techniques include, but are not limited to PCR amplification, STR analysis, DNA sequencing and genetic identity testing.

Further, existing quantitation systems are not easily automatable and frequently are sensitive to contaminants remaining in the DNA preparation. Because of the large number of samples projected to be analyzed and databased, a high throughput process linking conventional STR-based steps is desirable without sacrificing low throughput needs. A system for isolating DNA from samples that quantitates the DNA in the process of purification would eliminate a process step and would be a significant advance in the art. A process less sensitive to artifacts than conventional quantitation techniques would also be desirable.

SUMMARY OF THE INVENTION

The present invention permits adsorption of a DNA target material from a medium to a solid phase under defined condition, and transfer of defined quantities of the biological material into a second solution. Target DNA transferred into the second solution according to the present method can be used as templates for sequencing or as templates for amplification reactions without a separate quantitation step. Because this technique eliminates the requirement of separately quantitating isolated target material before downstream processing or analysis, the method saves time and lends itself to automation.

The present system involves isolation of DNA target material from other material in a cell sample using a magnetic particle based separation. This approach allows for flexibility in processing as the magnetic separation can be employed in either a low throughput manual format or a high throughput robotic format.

Briefly, in one aspect, the present invention comprises a method of isolating a defined quantity of a DNA target material from other material in a medium by (a) providing a medium including the DNA target material; (b) providing a discrete quantity of silica magnetic particles capable of reversibly binding a definable quantity of the DNA target material; (c) forming a complex of the silica magnetic particles and the DNA target material by combining the silica magnetic particles and the medium; (d) removing the complex containing the DNA target material from the medium by application of an external magnetic field; and (optionally) (e) separating the DNA target material from the complex by eluting the DNA target material, whereby a defined quantity of the DNA target material is obtained. Preferably, the quantity of DNA target material provided in step (a) is in excess of the reversible binding capacity of the particles. Depending on the subsequent application and the quantity of silica magnetic particles provided, the elution step may be unnecessary.

The above method may also be carried out using silica-containing solid supports other than silica magnetic particles. When using other silica-containing solid supports, the complex containing the DNA target material may be removed from the medium by a variety of methods, such as centrifugation or filtration.

A preferred practice of the method of the present invention comprises the following steps. A sample of a certain type of medium containing a DNA target material is mixed with magnetic particles in the presence of a chaotropic salt, wherein, the magnetic particles have a known or definable capacity for adsorbing the DNA target material from the type of medium. When the sample type is cells, the cells are lysed to release the DNA target material into solution, where it forms a complex with the particles. After washing away other cell components, the DNA target material may be eluted in a discrete volume resulting in a solution of defined DNA target material concentration. The present method is suitable for use in isolating DNA target material from a wide variety of different sample types, including but not limited to, whole blood, white blood cells, sperm cells, buccal cells, or bacterial cells. In a preferred embodiment, the amount of DNA present in the sample is in excess of the binding capacity of the particles. Such samples can be presented in any one of a number of different forms, including but not limited to, liquid form, freeze-dried, dried onto material found at a crime scene, or mounted on a solid support (e.g., cheek cells on a swab or blood cells on a paper filter). Additional steps may be employed, if necessary, to remove the cells from a solid support. The purified DNA target material may be stored in the elution solution or left attached to the magnetic particles. Thus, multiple samples of the DNA target material can be obtained and used when needed.

In another aspect, the present invention is a method of isolating a defined quantity of target DNA material from other materials in a medium using a preferred form of silica magnetic particle, i.e., a siliceous oxide-coated magnetic particle, wherein the preferred particles are capable of reversibly binding a definable quantity of the target DNA material per milligram of particle. This aspect of the invention comprises the following steps. A mixture is formed comprising the medium including the target DNA material, the siliceous oxide-coated magnetic particles, and a chaotropic salt. The salt concentration is sufficient to cause the target DNA material to adhere to the particles. The mixture is incubated, or allowed to remain in mixture, until DNA is adhered to the siliceous oxide-coated magnetic particles in the mixture. The siliceous oxide-coated magnetic particles are then removed from the mixture using a magnetic force. A defined quantity of the target DNA material is eluted from the siliceous oxide-coated magnetic particles by contacting the particles with an elution solution.

In a further aspect, the present invention is a kit for isolating a defined quantity of a DNA target material from a medium containing the same. The kit includes a discrete quantity of siliceous oxide-coated magnetic particles suspended in an aqueous solution in a first container, wherein the particles have the capacity to reversibly bind a definable quantity of the DNA target material from a medium for specific sample type. Optionally, the kit may include other components needed to isolate a defined quantity of DNA target material from a medium containing the same according to the methods of the present invention. For example, the kit may also contain a chaotropic salt in a second container and a wash solution in a third container and instructions.

Yet another aspect of the invention is a method of determining a calibration model for quantitating a DNA target material in a sample type of interest, the method comprising: (a) providing a first medium, wherein the first medium includes a discrete quantity of sample type of interest; (b) providing a second medium, wherein the second medium includes a different discrete quantity of sample type of interest; (c) mixing a first discrete quantity of silica magnetic particles with the first medium, wherein the silica magnetic particles are capable of reversibly binding a defined quantity of the DNA target material, thereby forming a first complex of the silica magnetic particles and the DNA target material from the first medium; (d) mixing a second discrete quantity of silica magnetic particles with the second medium, wherein the silica magnetic particles are capable of reversibly binding a defined quantity of the DNA target material, thereby forming a second complex of the silica magnetic particles and the DNA target material from the second medium; (e) removing the first complex from the first medium and the second complex from the second medium by application of an external magnetic field; (f) separately eluting the DNA target material from the first complex and second complex, producing a first eluent of isolated DNA target material from the first complex and a second eluent of isolated DNA target material from the second complex; (g) determining the amount of DNA target material in the first eluent and in the second eluent. Preferably, the first discrete quantity of particles provided in step (c) is the same quantity of particles as the second discrete quantity provided in step (d).

One calibration method, as illustrated in Example 3, involves determining the amount of particles necessary in the purification of target DNA from the smallest sample size (the smallest amount of DNA available) so that the DNA target material is present in excess, and the resulting purified target DNA is also in the desired target range. After determining the amount of particles desired from the smallest sample size, it is important to ensure that purification from the larger sample sizes also produces purified target DNA that is in the desired range of concentration or yield. This method generally determines the largest quantity of DNA that can be reliably obtained from the desired range of sample sizes, wherein the amount of target DNA obtained from each of the samples lies within the desired quantitative range of target DNA.

Another calibration method, as illustrated in Example 8, relies on using sample sizes that are known to contain a large excess of DNA target material, so that the range of particles used in the purification is known to be the factor limiting the quantity of DNA target material that is obtained. Using this method, a correlation is made between the highest and lowest quantity of target DNA that provides the desired utility for the application (in Example 8, this application is DNA sequencing), and the amount of particles used in the purification that results in the purification of target DNA quantities within the range desired for the application. When the target material is DNA, the amount of target material present in each eluent produced to construct the calibration model, as described above, is preferably determined by DNAQuant or PicoGreen analysis.

There are a variety of applications where this invention has utility. Two such areas include DNA sequencing, particularly automated DNA sequencing, and genetic analysis involving nucleic acid amplification reactions, such as the polymerase chain reaction (PCR). In each of these applications, the quantity of DNA target material must be kept within a well-defined range. Genetic analyses may include, for example, genetic identification used in forensics or paternity cases, and genetic analyses used in clinical laboratories. In such cases, it is helpful to have approximately the same quantity of DNA target material in each amplification reaction. Consistent quantity leads to consistent band intensity in a gel analysis and limited artifacts. The invention may also be used in conjunction with other amplification systems, such as transcription mediated amplification.

The present methods are readily adaptable to automation as, in a preferred practice, they allow for the simultaneous isolation and quantitation of DNA target material from multiple samples. For example, the present method could be used to isolate a defined quantity of target genomic DNA from blood or other tissue samples taken from multiple individuals in a population. Loci of interest, such as STR loci, of the isolated and quatitated genomic DNA could then be amplified and analyzed using any one of a number of known genetic analysis methods. See, for example, the GenePrints® STR analysis systems from Promega Corporation. When used as described immediately above to isolate, quantitate, and co-amplify multiple STR loci, such as the CODIS loci, in multiplex reactions (e.g., using the GenePrint® PowerPlex System from Promega) the amount of information in databases of such DNA typing results could be rapidly increased. The more data present in such databases, the more useful the databases are for identification of individuals, particularly for forensics applications.

The DNA target material isolated using the method of the present invention is sufficiently free of contaminating material for additional processing or analysis using standard molecular biology techniques. Applications of the present methods to isolate and quantitate various different DNA target materials from a variety of different media will become apparent from the detailed description of the invention below.

Other features, advantages and applications of the invention will become apparent to those skilled in the art upon review of the following detailed description and claims.

DETAILED DESCRIPTION OF THE INVENTION

Figure 1:
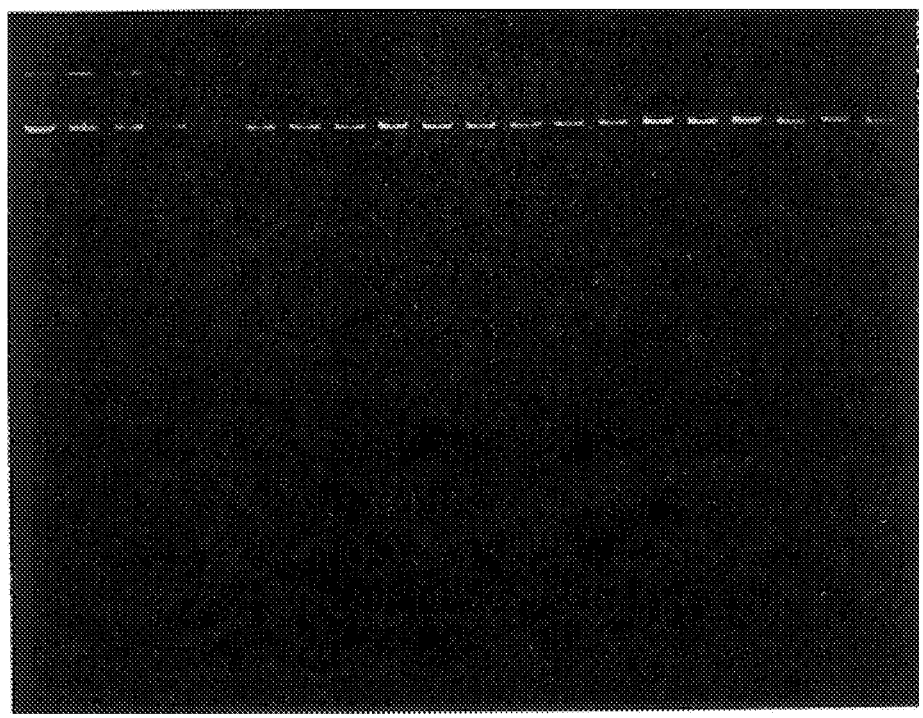
FIG. 1 shows a photograph of genomic DNA samples fractionated by gel electrophoresis and stained with ethidium bromide, wherein the samples of genomic DNA were isolated from different, discrete amounts of human whole blood, using nonporous MagneSil™ silica magnetic particles, as described in Example 3.

The present invention will now be described in detail, in part, by reference to the following definition of terms:

As used herein, the term "defined quantity" means the amount falls within a relatively narrow range. If the range is not known, then the range may be determined (i.e., a definable quantity) for a specific sample type and particle type as discussed below in the Detailed Description. The variation in the range results, in part, from limitations with the quantitation methods employed to build the calibration model.

"Sample type" means the form and source of the sample containing the DNA target material. Various sample types include, but are not limited to, liquid blood, dried blood on a solid support, such as paper or a swab, buccal cells, saliva, etc.

The term "DNA target material" refers to DNA including but not limited to plasmid DNA, genomic DNA, chromosomal DNA, DNA fragments produced from restriction enzyme digestion, amplified DNA produced by an amplification reaction such as the polymerase chain reaction (PCR) and single-stranded DNA.

The term "calibration model" refers to a set of data specific to particular reaction conditions, sample type and particle type which correlates the quantity of particles and sample to a defined quantity of DNA target material obtained from the purification.

The term "silica-containing solid support" means a solid support (such as silica paper or a silica membrane) comprising silica or a silica derivative, which is capable of reversibly binding a defined quantity of DNA target material. The silica may be coated on or incorporated within the solid support. Silica magnetic particles are a particularly preferred silica-containing solid support. Although the Detailed Description is directed to use of the highly preferred silica magnetic particles, the invention also contemplates a process employing other silica-containing solid supports.

The terms "isolate" and "isolated from" mean some contaminants are removed from the target material.

As used herein, the term "magnetic particles" refers to materials which have no magnetic field but which form a magnetic dipole when exposed to a magnetic field, i.e., materials capable of being magnetized in the presence of a magnetic field but which are not themselves magnetic in the absence of such a field. The term "magnetic" as used in this context includes materials which are paramagnetic or superparamagnetic. The term "magnetic", as used herein, also encompasses temporarily magnetic materials, such as ferromagnetic or ferrimagnetic materials with low Curie temperatures, provided that such temporarily magnetic materials are paramagnetic in the temperature range at which silica magnetic particles containing such materials are used according to the present methods to isolate biological materials.

Magnetic particles have been used for many years to isolate and purify polypeptide molecules such as proteins or antibodies. In recent years, however, magnetic particles and methods for using magnetic particles have been developed for the isolation of nucleic acid materials. Several different types of magnetic particles designed for use in nucleic acid isolation are described in the literature, and many of those types of particles are available from commercial sources. One such particle type is a magnetically responsive glass bead, preferably of a controlled pore size. See, e.g. Magnetic Porous Glass (MPG) particles from CPG, Inc. (Lincoln Park, N.J., U.S.A.); or porous magnetic glass particles described in U.S. Pat. Nos. 4,395,271; 4,233,169; or 4,297,337 which are herein incorporated by reference. Nucleic acid material tends to bind so tightly to glass, however, that it can be difficult to remove once bound thereto. Therefore, elution efficiencies from magnetic glass particles tend to be low compared to elution efficiencies from particles containing lower amounts of a nucleic acid binding material such as silica. A second type of magnetically responsive particles designed for use in direct binding and isolation of nucleic acids, are particles comprised of agarose embedded with smaller ferromagnetic particles and coated with glass. See, e.g. U.S. Pat. No. 5,395,498.

The term "silica magnetic particle" refers to a magnetic particle comprised of silica in the form of silica gel, siliceous oxide, solid silica such as glass or diatomaceous earth, or a mixture of two or more of the above. The term "silica gel" as used herein refers to chromatography grade silica gel, a substance which is commercially available from a number of different sources. Silica gel is most commonly prepared by acidifying a solution containing silicate, e.g. sodium silicate, to a pH of less than 10 or 11 and then allowing the acidified solution to gel. See, e.g. silica preparation discussion in *Kirk-Othmer Encyclopedia of Chemical Technology*, Vol. 6, 4th ed., Mary Howe-Grant, ed., John Wiley & Sons, pub., 1993, pp. 773–775. The term "silica magnetic particle" as used herein preferably refers to particles with the characteristics described above having the capacity to bind a definable quantity of DNA target material per milligram of silica magnetic particles. The silica magnetic particles used in the present invention preferably further comprise ferromagnetic material incorporated into a silica gel matrix.

The methods of this invention for isolating and quantitating DNA target material can be practiced using any silica-coated solid material capable of reversibly binding a definable quantity of the DNA target material. However, the methods of the present invention are preferably practiced using the siliceous oxide coated silica magnetic particles ("SOCM particles") disclosed in PCT publication number WO98/31840, which is herein fully incorporated by reference. The present invention is preferably practiced using silica magnetic particles having the following physical characteristics.

The silica magnetic particles used in the methods of this invention may be any of a number of different sizes. The type of particle used would be calibrated to determine its DNA binding capacity for a sample type. Smaller silica magnetic particles provide more surface area (one per weight unit basis) for adsorption, but smaller particles are limited in the amount of magnetic material which can be incorporated into such particles compared to larger particles. The median particle size of the porous silica magnetic particles used in the present invention is preferably about 1 to 25 microns, more preferably about 3 to 15 microns. The particle size distribution may also be varied. However, a relatively narrow particle size distribution is preferred. The particle size distribution is preferably such that about 80% by weight of the particles are within a 10 micron range about the median particle size, more preferably within an 8 micron range, and most preferably within a 6 micron range.

The magnetic particles of the present invention can be porous or non-porous. When the magnetic particles are porous, the pores are preferably of a controlled size range sufficiently large to admit the target nucleic acid material into the interior of the solid phase particle, and to bind to functional groups or silica on the interior surface of the pores. When the magnetic particles are porous silica magnetic particles, the total pore volume of each silica magnetic particle, as measured by nitrogen BET method, is preferably at least about 0.2 ml/g of particle mass. The total pore volume of porous silica magnetic particles particularly preferred for use as components of the pH dependent ion exchange matrix of the present invention, as measured by nitrogen BET, is preferably at least about 50% of the pore volume is contained in pores having a diameter of 600 Å or greater. A highly preferred porous silica magnetic particle has the following characteristics: an average particle diameter of about 5.0 to 8.5 microns, a BET surface area of about 18 to 55 microns/gm, and an acid leach resistance of less than about 7 ppm $Fe_2O_3$. Such particles are available as porous MagneSil™ particles from Promega Corporation.

The term "nonporous", is used herein to refer to silica magnetic particles used in the present invention which, if they have any pores at all, have much smaller pores than the porous silica magnetic particles described immediately above. Specifically, the pores of "nonporous" magnetic particles are too small to admit the DNA target material. Nonporous particles also have less surface area and less capacity to adsorb any given DNA target material, compared to porous particles of the same diameter. As a result of this difference, porous particles have a greater capacity to bind and release a greater amount of DNA target material than do nonporous particles, when the same gram weight of particles is used to isolate DNA target material from the same medium. However, DNA target material isolated using nonporous particles tends to contain fewer contaminants. A highly preferred nonporous silica magnetic particle has the following characteristics: an average particle diameter of about 14.5 microns, a BET surface area of about 3 microns/gm, and an acid leach resistance of less than about 2 ppm $Fe_2O_3$. Such particles are available as nonporous Magne-Sil™ silica magnetic particles from Promega Corporation.

At least two commercial silica magnetic particles are particularly preferred for use in the present invention, BioMag® Magnetic Particles from PerSeptive Biosystems, and the porous and nonporous MagneSil™ silica magnetic particles available from Promega Corporation.

"Complex" refers to silica magnetic particles or other silica-containing solid support having DNA target material adhered thereto. At least a portion of the DNA target material is capable of being released from the silica magnetic particles (i.e., reversibly binding) under appropriate conditions. The exact percentage of DNA target material released is not important as long as it is relatively consistent for a given set of reaction conditions.

The term "chaotropic salt" as used herein refers to salts of particular ions which, when present in a sufficiently high concentration in an aqueous solution, cause proteins present therein to unfold and nucleic acids to lose secondary structure. It is thought that chaotropic ions have these effects because they disrupt hydrogen-bonding networks that exist in liquid water and thereby make denatured proteins and nucleic acids thermodynamically more stable than their correctly folded or structured counterparts. Chaotropic ions include guanidinium, iodide, perchlorate, and trichloroacetate. Chaotropic salts include guanidine hydrochloride, guanidine thiocyanate (which is sometimes referred to as guanidine isothiocyanate), sodium iodide, sodium perchlorate, and sodium trichloroacetate.

The method of simultaneously isolating and quantitating DNA target material may be practiced as follows. The first step is to construct a calibration model for use in determining the amount of DNA target material expected to be obtained from a particular sample type using a discrete quantity of particles. Any given set of magnetic particles with a common set of physical characteristics have a defined capacity for adsorption of DNA target material, per milligram of particle, under the same conditions. Specifically, for a given set of reaction conditions (including the quantity of silica magnetic particles), the same amount of DNA target material is obtained from a specific sample type when the DNA is in excess over the binding capacity of the amount of particles used. Thus, the step of constructing a calibration model need only be performed once for a given set of reaction conditions, sample type and particle type.

After the calibration model is constructed, the DNA target material is isolated from the same type of medium under the same solution conditions and using the same type of particles used to acquire the calibration model.

When the DNA target material to be isolated is present in cells, the cells are preferably disrupted in the presence of a lysis buffer, which releases the DNA target material into the lysis buffer. When the DNA target material is a nucleic acid target material contained within cells, the cells are preferably lysed in a lysis solution which separates protein and other materials in solution from the nucleic acid, while promoting adsorption of the nucleic acid to silica magnetic particles when combined therewith. The particles with the target material attached may be separated from other cell material using a magnetic field, and the particles may be washed. The nucleic acid target material may then be eluted into a discrete volume of water or other elution solution to give a defined quantity of DNA target material.

In order to obtain a representative calibration model, actual sample analysis should occur under the same reaction conditions used to develop the calibration model. These conditions include the following: sample type, particle type, solution conditions on combination with the magnetic particles, wash procedure including the composition of any wash solution, the composition of any elution solution, and the temperature at which the various method steps are carried out. The reaction conditions may be optimized by experimentation. However, for purposes of the present method, consistency in reaction conditions is more important than optimization.

The calibration model may be acquired as follows. A lysis buffer may be added to lyse sample cells and release the DNA target material so that it is free to complex with the silica magnetic particles. To various known or measured amounts of a sample type to be analyzed, a discrete (known and preferably constant) quantity of silica magnetic particles is added. The lysis buffer may be added before, during or after adding the magnetic particles to the sample. For liquid whole blood the lysis buffer is added to the sample prior to, or together with, the silica-coated magnetic particles. Preferably, the lysis buffer is added to the sample together with the silica-coated magnetic particles. The silica magnetic particles are combined with the lysed cells under conditions wherein a complex of the particles and DNA target material is formed.

The complex of the DNA target material and silica magnetic particles is separated from the lysate solution in the presence of a magnetic field, whereupon the lysate solution is removed and discarded. The remaining complex is preferably washed at least once to remove additional contaminants. After the final washing step, if washing steps are included, the DNA target material is eluted from the complex by adding a known volume of elution solution to the complex, and separating the particles from the elution solution in a magnetic field. Preferably the elution solution is water. A known volume of the solution containing the eluted DNA target material may then be further analyzed, e.g. amplified, electrophoresed on a gel or quantitated by known methods. Based on the quantitation results, the total quantity of isolated DNA target material in the eluted solution can be determined. This data provides information on the quantity of DNA target material reversibly bound to the particles for various quantities of sample of a particular sample type.

As an additional amount of any given sample of a medium is added to a discrete quantity of particles, the quantity of DNA target material isolated therefrom will increase until the particles reach a saturation point. Upon approaching the saturation point, the quantity of DNA target material obtained will not significantly increase as additional sample is provided. When the DNA target material is present in excess of the binding capacity of the particles, excess sample and excess DNA target material will simply be washed away. Preferably, the DNA target material is present in excess of the binding capacity of the particles. Thus, under the same conditions, and provided the DNA is present in excess of the binding capacity of the particles, the same quantity of particles will isolate and release approximately the same amount of DNA from a sample type regardless of the sample size.

At low sample concentrations, it is helpful to add very small, controlled amounts of particles so DNA concentration is in slight excess of the binding capacity. The binding capacity of different particles will vary, but need only be determined once for a particular particle type, sample type and reaction conditions (e.g. by a test like that described in Example 7). Because of the control in the quantity of DNA isolated from a particular sample, overamplified signals can be avoided.

Example 1 describes a method of determining a calibration model. Example 1 shows the saturation point or the capacity of nonporous silica magnetic particles (in quantities of either 500 $\mu$g or 700 $\mu$g) to reversibly bind DNA from liquid human blood. Example 1 shows that a 4-fold increase in blood resulted in an increase in isolated DNA much less than 4-fold. Like Example 1, Example 3 shows how a calibration model is obtained with much larger sample sizes (200 $\mu$l to 1 ml of whole blood). In Example 3, DNA is clearly in great excess of the reversible binding capacity of the particles. Thus, the saturation point has been reached and the yield is relatively consistent over a wide range of sample volumes when using volumes in excess of the saturation point. These DNA samples are concentrated enough to quantify by spectrophotometry. The $A_{260}/A_{280}$ data shows high sample purity using the process of the invention. Calibration models like those in Examples 1 and 3 show that a relatively narrow range of DNA target material may be isolated and quantitated for a given sample type by holding process conditions constant and controllably varying the quantity of sample and particles.

For purposes of genomic typing analyses such as STR, the exact quantity of DNA target material isolated is not critical as long as the amount falls within a range usable for analysis. This range depends on the system employed. For example, amplification using Promega's GenePrint® PowerPlex™ 1.1 system should be performed using between about 0.5 and 5 ng of DNA per assay (preferably about 1 ng DNA) to avoid overamplification and obtain samples that are readily genotyped. Therefore, by comparing the calibration model to the usable range for the system employed, the quantity of sample and particles needed to isolate a usable amount of DNA target material may be determined prior to isolating the DNA target material from the sample of interest.

Based on instructions and protocol from the manufacturer of the system into which the sample will be placed for analysis, the desired sample range can be determined. Therefore, to obtain a desirable quantity of DNA target material, a calibration model can be employed to determine appropriate parameters such as the quantity of particles, quantity of sample, and an appropriate volume or fraction of the total isolated DNA target material.

The DNA target material isolated and quantitated using the method of the present invention can be obtained from eukaryotic or prokaryotic cells in culture or from cells taken or obtained from tissues, multicellular organisms including animals and plants; body fluids such as blood, lymph, urine, feces, or semen; embryos or fetuses; food stuffs; cosmetics; or any other source of cells. Certain species of DNA are isolated according to the present method from the DNA of organelles, viruses, phages, plasmids, viroids or the like that infect cells. Cells will be lysed and the lysate usually processed in various ways familiar to those in the art to obtain an aqueous solution of DNA, to which the separation or isolation methods of the invention are applied. The DNA in such a solution will typically be found with other components, such as proteins, RNAs or other types of components.

The DNA target material may come from a sample on a solid support, such as filter paper. DNA target material may be removed from the solid support by placing at least a portion of the sample on the solid support in a solution containing a chaotropic salt (see Examples 4–5). To facilitate removal of the DNA target material from the solid support, the temperature of the solution is preferably in the range of about 60° C. to 100° C., most preferably in the range of about 90° C. to 100° C. Preferably, the chaotropic salt solution also includes a pH buffer.

Regardless of the nature of the source of such material, the DNA target material to be isolated in the present methods is provided in a medium comprising the DNA target material and other species. The DNA target material must be present in the medium in a form in which it is available to adhere to the silica magnetic particles. When the DNA target material is contained inside a cell, the cell walls or cell membrane can make the material unavailable for adhesion to the particles. Even if such cells are lysed or sufficiently disrupted to cause the DNA target material contained therein to be released into the surrounding solution, cellular debris in the solution could interfere with the adhesion of the target material to the silica magnetic particles. Therefore, in cases where the target material to be isolated using the methods of the present invention is contained within a cell, the cell is preferably first processed by lysing or disrupting the cell to produce a lysate, and more preferably additionally processed by clearing the lysate of cellular debris (e.g., by centrifugation or vacuum filtration) which may interfere with adhesion of the target material to silica magnetic particles when present in the medium.

Any one of a number of different known methods for lysing or disrupting cells to release DNA materials contained therein is suitable for use in producing a medium from cells for use in the present invention. The method chosen to release the DNA material from a cell will depend upon the nature of the cell containing the material. For example, in order to cause a cell with a relatively hard cell wall, such as a fungus cell or a plant cell, to release the nucleic acid material contained therein one may need to use harsh treatments such as potent proteases and mechanical shearing with a homogenizer or disruption with sound waves using a sonicator. Contrastingly, DNA material can be readily released from cells with lipid bi-layer membranes such as *E. coli* bacteria or animal blood cells merely by suspending such cells in an aqueous solution and adding a detergent to the solution.

Once the DNA material is released from cells lysed or disrupted as described above, cellular debris likely to interfere with the adhesion of the DNA material to silica magnetic particles can be removed using a number of different known techniques or combination of techniques. The solution of lysed or disrupted cells is preferably centrifuged to remove particulate cell debris. Optionally, the supernatant may then be further processed by adding a second solution to the supernatant which causes a precipitate of additional other material to form, and then removing the precipitate from the resulting solution by centrifugation.

When the DNA material of interest is plasmid DNA initially contained in an *E.coli* bacterial cell, the DNA material is preferably released from the bacteria cell by addition of an alkaline solution, such as a solution of sodium hydroxide, to form a lysate. A neutralizing solution, such as an acidic buffer, is preferably added to the resulting supernatant to form a precipitate of additional potentially interfering material. The precipitate thus formed is preferably removed by centrifugation or filtration. The remaining supernatant of cleared lysate is the medium containing the DNA material of interest.

The medium provided in the first step of the method of this invention need not contain nucleic acid material released directly from cells. The nucleic acid material can be the product of an amplification reaction, such as amplified DNA produced using the polymerase chain reaction (PCR). The nucleic acid material can also be in the form of fragments of DNA produced by digesting DNA with a restriction enzyme. The medium can also be in the form of a mixture of melted or enzymatically digested electrophoresis gel and nucleic acid material. Upon freeing the biological target from surrounding cell components, the DNA target material is free to adhere to silica magnetic particles.

A complex of the silica magnetic particles and the DNA target material is formed by exposing the particles to the medium containing the DNA target material under conditions designed to promote the formation of the complex. The complex is preferably formed in a mixture of the silica magnetic particles, the medium, and a chaotropic salt.

The concentration of chaotropic ions in the mixture formed in this practice of the present method is preferably between about 0.1 M and 7.0 M, but more preferably between about 0.8 M and 4.5 M. The concentration of chaotropic ions in the mixture must be sufficient to cause the DNA target material to adhere to the silica magnetic particles in the mixture, but not so high as to irreversibly denature, degrade, or to cause the target material to precipitate out of the mixture. Large molecules of double-stranded DNA, such as chromosomal DNA, are stable at chaotropic salt concentrations between 0.5 and 2 molar, but are known to precipitate out of solution at chaotropic salt concentrations above about 2 molar. See, e.g. U.S. Pat. No. 5,346,994 issued to Piotr Chomczynski, column 2, lines 56–63. Contrastingly, smaller molecules of DNA such as plasmid DNA, restriction or PCR fragments of chromosomal DNA, or single-stranded DNA remain undegraded and in solution at chaotropic salt concentrations between 2 and 5 molar.

With any chaotropic salt used in the invention, it is desirable that the concentration of the salt, in any of the solutions in which the salt is employed in carrying out the invention, remain below the solubility of the salt in the solution under all of the conditions to which the solution is subjected in carrying out the invention.

In a practice of the present methods, the mixture of medium and sample is incubated until at least some of the DNA target material is adhered to the silica magnetic particle to form a complex. This incubation step is carried out at a temperature of at least 0C., preferably at least 4° C., and more preferably at least 20° C., provided that the incubation temperature is no more than 67° C. The incubation step must be carried out at a temperature below the temperature at which the silica magnetic particles begin to loose their capacity to reversibly bind the nucleic acid material. The incubation step is most preferably carried out at about room temperature (i.e. at about 25° C.).

When the DNA target material is contained within a cell, it is desirable to lyse the cells in a lysis solution containing the chaotropic salt so that cell lysis and complex formation may be achieved with the same solution.

In addition to the chaotropic salt, the lysis solution may contain dipolar or nonionic detergents such as CHAPS [3-[3-cholamidopropyldimethylammonio]-1-propane sulfonate] or Triton X-100 (Sigma, St. Louis, Mo.). Preferably, the lysis solution includes a pH buffer to stabilize the pH at approximately 7.0 in order to keep the DNA structurally intact. The lysis solution may also contain a divalent cation chelator, such as EDTA. This lysis solution is also useful for removing DNA target material from a solid support.

After forming a complex, the complex is removed from the mixture using a magnetic field. Other forms of external force in addition to the magnetic field can also be used to isolate the DNA target material according to the methods of the present invention after the initial removal step. Suitable additional forms of external force include, but are not limited to, gravity filtration, vacuum filtration and centrifugation.

The external magnetic field used to remove the complex from the medium can be suitably generated in the medium using any one of a number of different known means. For example, one can position a magnet on the outer surface of a container of a solution containing the particles, causing the particles to migrate through the solution and collect on the inner surface of the container adjacent to the magnet. The magnet can then be held in position on the outer surface of the container such that the particles are held in the container by the magnetic field generated by the magnet, while the solution is decanted out of the container and discarded. A second solution can then be added to the container, and the magnet removed so that the particles migrate into the second solution. Alternatively, a magnetizable probe could be inserted into the solution and the probe magnetized, such that the particles deposit on the end of the probe immersed in the solution. The probe could then be removed from the solution, while remaining magnetized, immersed into a second solution, and the magnetic field discontinued permitting the particles go into the second solution. Any source of magnetic force sufficiently strong to separate the silica magnetic particles from a solution would be suitable for use in the nucleic acid isolation methods of the present invention. Magnetic separation devices are commercially available. See, e.g. MagneSphere® Technology Magnetic Separation Stand or the PolyATract® Series 9600™ Multi-Magnet, both available from Promega Corporation; MagneTight Separation Stand (Novagen, Madison, Wis.); or Dynal Magnetic Particle Concentrator (Dynal, Oslo, Norway). The magnetic force is preferably provided in the form of a magnetic separation stand, such as one of the MagneSphere® Technology Magnetic Separation Stands (Catalog Nos. Z5331 to 3, or Z5341 to 3) from Promega Corporation.

The present invention provides convenient and efficient means for isolating DNA target material of interest from a variety of different sample types. A preferred aspect of the present method described briefly above, wherein magnetic force is used to remove the particles from the media, offers significant advantages over conventional isolation methods wherein a DNA target material is reversibly bound to other silica material. Specifically, the magnetic removal step of the method substitutes for vacuum filtration or centrifugation steps required in conventional silica binding and elution isolation methods. It is, therefore, particularly amenable to being automated.

In a preferred aspect of the methods of the present invention, the complex removed from the medium is washed at least once by being rinsed in a wash solution. Washing removes additional impurities, which include anything other than the DNA target material of interest. The wash solution used in this preferred additional step of the method preferably comprises a solution capable of removing contaminants from the silica magnetic particle. The wash solution preferably comprises a salt and a solvent, preferably an alcohol. The alcohol facilitates evaporation of the wash solution. The concentration of alcohol in this last preferred form of the wash solution is preferably at least 30% by volume, more preferably at least 40% by volume, and most preferably at least 50% by volume. The alcohol so used is preferably ethanol or isopropanol or mixtures thereof, more preferably ethanol. The salt is preferably in the form of a buffer, and most preferably in the form of an acetate buffer. The concentration of salt in the wash solution is sufficiently high to ensure the nucleic acid material is not eluted from the silica magnetic particles during the wash step(s).

The complex is preferably washed after removal from the medium by resuspending the complex in the wash solution. The complex is preferably removed from the wash solution after the first wash, and washed at least once more, and most preferably three more times using fresh wash solution for every wash step.

A definable quantity of DNA target material is available in the complex. In some analyses or molecular biology processing procedures, small quantities of magnetic particles will not poison or significantly interfere with the process. Thus, in appropriate processes, the complex may be processed directly without first separating the DNA target material from the silica magnetic particles.

Preferably, however, the DNA target material is eluted from the silica magnetic particles before further processing. This may be achieved by exposing the complex to an elution solution. The elution efficacy (or the percentage of bound DNA target material to be removed from the particles) is not important. As long as a relatively consistent percentage elutes for a given set of reaction conditions, particle type and sample type. As long as a defined amount of DNA target material can consistently adsorb to the particles and elute off, then quantitation may be performed.

The elution solution is preferably an aqueous solution of low ionic strength, more preferably water or a low ionic strength buffer at about a pH at which the nucleic acid material is stable and substantially intact. Any aqueous solution with an ionic strength at or lower than TE buffer (i.e. 10 mM Tris-HC1, 1 mM ethylenediamine-tetraacetic acid (EDTA), pH 8.0) is suitable for use in the elution steps of the present methods, but the elution solution is preferable buffered to a pH between about 6.5 and 8.5, and more preferably buffered to a pH between about 7.0 and 8.0. TE Buffer and distilled or deionized water are particularly preferred elution solutions for use in the present invention. The low ionic strength of the preferred forms of the elution solution described above ensures the nucleic acid material is released from the particle. Other elution solutions suitable for use in the methods of this invention will be readily apparent to one skilled in this art. The DNA target material eluted from the complex in the elution step of the method is preferably separated from the silica magnetic particles The DNA target material eluted using the method of the present invention is suitable, without further isolation, for analysis or further processing by molecular biological procedures. Eluted DNA can be analyzed by, for example, sequencing, restriction analysis, or nucleic acid probe hybridization. Thus, the methods of the invention can be applied as part of methods, based on analysis of DNA, for, among other things, diagnosing diseases; identifying pathogens; testing foods, cosmetics, blood or blood products, or other products for contamination by pathogens; forensic testing; paternity testing; and sex identification of fetuses or embryos. Preferably, eluted genomic DNA is analyzed in a DNA typing process. For example, once purified, the DNA is ready for use with the conventional amplification and DNA typing systems. PowerPlex™ 1.1 and PowerPlex™ 2.1 systems (Promega) provide amplification of the 13 core CODIS loci plus the gender identification locus, amelogenin, and the low stutter pentanucleotide repeat locus Penta E in a two-tube amplification system. These two systems have three loci in common to guard against sample mix-up.

The eluted DNA provided by the method of the invention can be further processed in a number of ways, e.g. sequencing, transcription, enzyme reactions. Restriction fragments from the eluted DNA can be ligated into vectors and transformed into suitable hosts for cloning or expression. Segments of the eluted DNA can be amplified by any of the various methods known in the art for amplifying target nucleic acid segments. If eluted DNA is a plasmid or another type of autonomously replicating DNA, it can be transformed into a suitable host for cloning or for expression of genes on the DNA which are capable of being expressed in the transformed host.

The components needed to perform the method of the invention may be placed in a kit for isolating a known quantity of a DNA target material from a medium. At a minimum, such a kit should contain: a discrete quantity of siliceous oxide-coated magnetic particles suspended in an aqueous solution in a first container, wherein the particles have the capacity to reversibly bind a definable quantity of the DNA target material from the medium for a sample type. Preferably, the kit also includes a chaotropic salt. The particles may be suspended in a solution with the chaotropic salt. Preferably, the kit also includes a wash solution.

For liquid blood and bloodstains (about 5 μl to 10 mL of blood), a suitable kit may include the following components: a lysis buffer, a wash buffer, silica magnetic particles, and, optionally, an elution solution and/or a magnetic stand.

Preferably, the lysis solution doubles as a wash solution. A high throughput system could include the components listed above plus a 96-well plate.

A suitable kit for plasmid purification may contain: a cell resuspension solution, a lysis solution, a neutralization solution, silica magnetic particles, a wash solution, and an elution solution.

The following, non-limiting examples teach various embodiments of the invention. In the examples, and elsewhere in the specification and claims, volumes, pH and concentrations are at room temperature unless specified otherwise. Only the most preferred forms of the silica magnetic particles was used in each of the examples below, i.e. porous and nonporous MagneSil™ particles. However, one skilled in the art of the present invention will be able to use the teachings of the present disclosure to select and use forms of the silica magnetic particles other than the porous and nonporous MagneSil™ particles whose use is illustrated in the aspects of the methods of the present invention demonstrated in the Examples below.

EXAMPLES

The following examples are provided to illustrate various aspects of the invention, without limiting the scope thereof:

Example 1

DNA Isolation From Blood Using Nonporous MagneSil™ Silica Magnetic Particles

In this example, different amounts of nonporous MagneSil™ silica magnetic particles (Promega Corp.) were used to isolate DNA from human blood samples of varying size. Blood was collected in an EDTA-coated vacutainer tube and stored at 4° C. until used (under two weeks). Varying amounts of liquid blood, between 6 μl and 25 μl as listed in Table 1, were placed in 1.5 ml conical tubes. Then 100 μl of a solution containing 93 μl Lysis Buffer (4.5 M guanidine thiocyanate, 1% Triton X-100, 1% CHAPS [3-[3-cholamidopropyldimethylammonio]-1-propane sulfonate], 10 mM EDTA, 10 mM Tris pH 7.3, adjusted to pH 6.8–7.0) and either 5 μl or 7 μl water containing 100 μg/,l nonporous MagneSil™ silica magnetic particles were added. The solutions were vortexed briefly. Then the tubes were incubated at room temperature for 5 minutes, vortexed briefly and placed on a magnetic stand (Promega) to separate the particles from the solution. The solution was carefully removed and 100 μl wash buffer (100 mM NaCl, 25% ethanol, 25% isopropyl alcohol) was added. The tubes were then removed from the magnetic stand, vortexed briefly and returned to the magnetic stand. The wash solution was removed and the wash was repeated two more times for a total of three washes. After removing the final wash, the particles were allowed to air dry at room temperature for 5 minutes. The tubes were removed from the magnetic stand and 100 μl water was added and the tubes were vortexed briefly. The tubes were placed at 60° C. for five minutes, vortexed briefly and then placed on the magnetic stand. The DNA solution was removed and stored in a 0.5 ml conical tube.

Table 1 shows the total amount of DNA obtained from between 6 and 25 μl liquid blood using either 500 or 700 μg of nonporous MagneSil™ silica magnetic particles. The DNA concentration was determined using PicoGreen DNA dye as per the manufacturer's recommendations (Molecular Probes, Eugene, Oreg.). Both MagneSil™ silica magnetic particle amounts used demonstrated approximately saturation kinetics. The 500 μg amount was approaching saturation and the 700 μg amount was slightly less than saturation. The variation in the amount of DNA isolated was significantly less than the variation in the range of volume of blood, especially between the 10 and 25 μl volumes of blood.

TABLE 1

| Volume of Blood (μl) | DNA eluted (ng) | |
|---|---|---|
| | 500 μg particles | 700 μg particles |
| 6 | 68 | 78 |
| 6 | 60 | 69 |
| 8 | 74 | 66 |
| 8 | 79 | 91 |
| 10 | 85 | 106 |
| 10 | 84 | 106 |
| 15 | 87 | 121 |
| 15 | 79 | 119 |
| 20 | 124 | 123 |
| 20 | 96 | 118 |
| 25 | 96 | 146 |
| 25 | 110 | 170 |

Example 2

Isolated DNA Analyzed

In this example, the DNA prepared in Example 1 was used to analyze for the identity of the allele present at 8 short tandem repeat (STR) loci. One microliter samples of the DNAs purified from the blood samples using 700 μg of nonporous MagneSil™ silica magnetic particles (Promega) as described in Example 1 were amplified using Promega's GenePrint® PowerPlex™ 1.1 System (Promega #DC6091) according to manufacturer's instructions. It is recommended that between 0.5 and 5 ng of DNA be used per assay with this system, with the most preferred amount being 1 ng DNA.

One microliter of the amplification product was loaded onto a denaturing polyacrylamide gel and electrophoresed as described in the GenePrints PowerPlex™ 1.1 System Technical Manual. The gel was scanned using an FMBIO® II fluorescent scanner (Hitachi, South San Francisco, Calif.). Peak heights were determined and normalized for each observed allele. The data points represent the mean of the 15 alleles for each sample, with the heights for the combined alleles generated from the DNA prepared from 10 μl blood sample set to equal one. These data points and the standard deviation are listed below in Table 2. The peak heights only varied by about two-fold and were nearly identical from samples of 10 to 25 μl of blood. The data demonstrated that all samples were easily genotyped.

TABLE 2

| Soln. | DNA Prepared From Amount of Blood | Average Normalized Peak Height | Std Deviation |
|---|---|---|---|
| 1 | 6 μl | 0.52 | 0.15 |
| 2 | 8 μl | 0.70 | 0.12 |
| 3 | 10 μl | 1.0 | 0.11 |
| 4 | 15 μl | 1.04 | 0.23 |
| 5 | 20 μl | 1.01 | 0.26 |
| 6 | 25 μl | 1.17 | 0.21 |

Example 3

Nonporous Silica Magnetic Particles and Guanidine Thiocyanate

In this example, genomic DNA was purified from human whole blood. The blood had been drawn the previous day in an EDTA-coated vacutainer and then stored at 4° C. All purifications were performed in triplicate, and all steps and incubations were at room temperature and pressure unless otherwise specified. Magnetic clearing of blood lysate and purification of genomic DNA used solutions from Promega's Wizard™ Genomic DNA Purification kit, (A1620) and nonporous silica magnetic particles using guanidine thiocyanate.

One ml, 800 μl, 600 μl, 400 μl, and 200 μl of blood were placed in separate 15 ml tubes containing 3.0 ml of Wizard Genomic Cell Lysis solution, mixed, and incubated for 10 minutes. The tubes were then centrifuged at 800×g for 10 minutes. The solution was removed, leaving the white blood cell (wbc) pellet at the tube bottom.

The wbc pellet was vortexed and 1.0 ml of Nuclei Lysis solution was added. Then the tube was vortexed and incubated for 1 hour at 37° C. Then 330 ul of Wizard™ Genomic Protein Precipitation solution was added and the tubes vortexed and centrifuged at 800×g for 10 minutes. The solutions were removed from the tubes and transferred to clean tubes containing 100 μl (100 mg/ml) non-porous MagneSil™ silica magnetic particles, and the solutions were vortexed.

Two milliliters of 5 M guanidine thiocyanate (GTC) was added, the tube was mixed and then incubated for 2 minutes. The tube was then placed on a magnetic rack for 5 minutes. The solution, separated from the particles, was removed and discarded. Five ml of SV Total RNA Column Wash (Promega, Z3100) was added, the tube was vortexed for 5 seconds, and the tube was again placed on a magnetic rack for 2 minutes. Then the solution, separated from the particles, was removed and discarded. The wash was repeated. A final wash was performed using 5.0 ml of 80% ethanol. The tube was vortexed for 5 seconds, and placed on a magnetic rack for 2 minutes. The solution, separated from the particles, was removed and discarded. The 80% ethanol wash was repeated twice for a total of three washes. The tubes were then air dried for 60 minutes in the magnetic rack. After removal from the magnetic rack, DNA on the particles was eluted into 400 ul of Wizard™ Genomic Renaturation Solution for 5 minutes. The tube was then again placed on a magnetic rack for 5 minutes and the solution containing DNA was removed to a clean tube.

The DNA purification results were obtained by spectrophotometric analysis (DNA diluted 1:2 in sample buffer) by PicoGreen analysis according to manufacturer's instructions (Molecular Probes) and by DNAQuant analysis according to manufacturer's instructions (Promega Corp.) and are listed below in Table 3. The results are also shown in FIG. 1. Lanes 1–5 correspond, respectively, to 100, 80, 60, 40 and 20 ng Promega genomic DNA standard Part #6304A. Lanes 6 and above were loaded with 10 μl of sample.

TABLE 3

| blood (μl) | A260 | A280 | A260/ 280 | Yield, μg | PicoGreen DNA | | Lane on Gel |
|---|---|---|---|---|---|---|---|
| | | | | | (μg) | Quant(μg) | |
| 200 | 0.0643 | 0.0287 | 2.2371 | 2.57 | 1.3 | 1.9 | 20 |
| 200 | 0.0646 | 0.0285 | 2.2632 | 2.58 | 1.3 | 1.8 | 19 |
| 200 | 0.0620 | 0.0273 | 2.2702 | 2.48 | 1.1 | 1.8 | 18 |
| 400 | 0.0898 | 0.0423 | 2.1213 | 3.59 | 2.0 | 2.6 | 17 |
| 400 | 0.0875 | 0.0415 | 2.1088 | 3.50 | 1.9 | 2.6 | 16 |
| 400 | 0.0889 | 0.0418 | 2.1242 | 3.55 | 1.8 | 2.6 | 15 |
| 600 | 0.0769 | 0.0355 | 2.1653 | 3.07 | 1.6 | 1.8 | 14 |
| 600 | 0.0752 | 0.0335 | 2.2423 | 3.00 | 1.5 | 1.9 | 13 |

TABLE 3-continued

| blood (µl) | A260 | A280 | A260/ 280 | Yield, µg | PicoGreen DNA (µg) | Quant(µg) | Lane on Gel |
|---|---|---|---|---|---|---|---|
| 600 | 0.0748 | 0.0337 | 2.2175 | 2.99 | 1.5 | 2.2 | 12 |
| 800 | 0.0950 | 0.0447 | 2.1255 | 3.80 | 1.6 | 2.2 | 11 |
| 800 | 0.0823 | 0.0373 | 2.2047 | 3.29 | 1.9 | 2.4 | 10 |
| 800 | 0.0868 | 0.0403 | 2.1536 | 3.47 | 2.0 | 2.6 | 9 |
| 1.0 ml | 0.0739 | 0.0330 | 2.2353 | 2.95 | 1.9 | 2.3 | 8 |
| 1.0 ml | 0.0686 | 0.0304 | 2.2557 | 2.74 | 1.5 | 2.0 | 7 |
| 1.0 ml | 0.0747 | 0.0338 | 2.2047 | 2.98 | 1.7 | 2.4 | 6 |

With the spectrophotometric analysis, the average yield was 3.11 µg. The lowest value was 2.48 or 79.8% of average. The highest value was 3.8 or 122.3% of average. With the PicoGreen analysis, further illustrated in FIG. 1, the average yield is 1.6 µg. The lowest value was 1.1 or 33% of average, while the highest value was 2.0 or 20% from the average. So all samples are within 33% of the average. With the DNAQuant assay, the lowest value was 1.8, while the hightest value was 2.6. The A260/A280 values are higher than the 1.7–1.9 desired range and might reflect the presence of residual contaminants.

Example 4

DNA Isolation From S&S 903 Paper Stained With Blood

In this example, it was demonstrated that the following procedure using Lysis Buffer, as described in Example 1, released DNA from blood dried on to S&S 903 paper (Schleicher & Schuell). Nonporous silica magnetic particles were then subsequently used to purify the released DNA. Human bloodstains on S&S 903 paper, ranging from 14 mm$^2$ to 100 mm$^2$ in size and containing from 5 µl to 50 µl of blood respectively, were cut out and placed in the bottom of 1.5 ml conical tubes. Then 100 µl Lysis Buffer, as described in Example 1, was added to the tubes containing 50 mm$^2$ or less S&S 903 paper and 200 µl of Lysis Buffer was added to 100 mm$^2$ S&S 903 paper. The tubes were then placed at 95° C. for 30 minutes. The tubes were then removed from the heat source and the paper removed with a sterile pipette tip. Excess liquid was removed from the paper by pressing the paper against the side of the tube with the pipette tip. Then 7 µl water, containing 700 µg nonporous MagneSil™ silica magnetic Particles, was added and the tube mixed by gentle vortexing. The remainder of the DNA purification procedure was performed as described in Example 1.

One microliter of DNA purified from each of the bloodstains was amplified with GenePrint® PowerPlex™ 1.1 System as described in Example 2. One microliter of the amplification product was loaded onto a denaturing gel and electrophoresed as described in the GenePrint® PowerPlex™ 1.1 System Technical Manual. The gel was scanned using an FMBIO® II fluorescent scanner (Hitachi, South San Francisco, Calif.). Peak heights were determined and normalized for each observed allele. The data points listed in Table 4 below, represent the mean of the 15 alleles for each sample and their standard deviations, with the heights for the combined alleles generated from the DNA prepared from 10 µl blood sample set to equal one. The mean normalized peak heights for each sample were all within 5% indicating that the amplifications were uniform regardless of whether the DNA had been isolated from the 5, 10, 25, or 50 µl blood stain.

TABLE 4

| Soln. | DNA Prepared From Amount of Blood | Average Normalized Peak Height | Std Deviation |
|---|---|---|---|
| 1 | 5 µl | 1.05 | 0.07 |
| 2 | 10 µl | 1.0 | 0 |
| 3 | 25 µl | 1.05 | 0.14 |
| 4 | 50 µl | 0.95 | 0.12 |

Table 5 below lists the standard deviation between peak heights within each sample. The deviation was consistently between 16 and 20%, indicating that small and large alleles were being amplified uniformly regardless of sample size.

TABLE 5

| Soln. | DNA Prepared From Amount of Blood | Std. Deviation |
|---|---|---|
| 1 | 5 µl | 0.16 |
| 2 | 10 µl | 0.16 |
| 3 | 25 µl | 0.21 |
| 4 | 50 µl | 0.17 |

Example 5

DNA Isolation From FTA™ Paper Stained With Blood

In this example, it is shown that DNA attached to FTA™ Paper (Life Technologies, Inc., Gaithersburg, Md.) was released from the paper with the use of the Lysis Buffer described in Example 1. The released DNA was then subsequently purified with nonporous MagneSil™ silica magnetic particles and used for STR analysis.

The indicated size of FTA™ paper (113 mm$^2$, 57 mm$^2$, and 28 mm$^2$) stained with human blood was heated at 95° C. for 30 minutes in 100 µl Lysis Buffer as described in Example 2. The paper and the solution were placed in a spin basket (Millipore, Bedford, Mass.) without a filter and centrifuged in a microcentrifuge for 2 minutes at 14,000 rpm. Then 700 µg of nonporous MagneSil™ silica magnetic particles in 7 µl water were added to the tube, vortexed briefly, and incubated for five minutes at room temperature. The tube was briefly vortexed and then placed on a magnetic stand (Promega Corp.) where the particles separated from the solution and the solution removed. The particles were washed three times with 100 µl wash buffer (described in Example 1). The particles were then air dried for 5 minutes at room temperature. Then 100 µl water was added to the tube with the particles and the tube was incubated at 60° C. for five minutes. The tube was briefly vortexed and then placed in a magnetic stand at room temperature and the DNA solution removed and stored at 4° C. One microliter of each solution was amplified using GenePrint® PowerPlex™ 1.1, the amplified product run on a denaturing gel and the gel analyzed on an FMBIO® II fluorescent scanner as described in Example 2. Peak heights were normalized and they are listed in Table 6 below. In this example, the data show that approximately equal amounts of DNA were purified from different amounts of blood-stained FTA™ paper when the amount of nonporous MagneSil™ silica magnetic particles used in the above protocol was kept constant.

TABLE 6

| Locus | Allele | Normalized Peak Heights | | |
|---|---|---|---|---|
| | | 113 mm² | 57 mm² | 28 mm² |
| CSF1PO | 12 | 0.80 | 1.97 | 1.00 |
| CSF1PO | 10 | 0.99 | 1.28 | 1.00 |
| TPOX | 10 | 0.55 | 1.09 | 1.00 |
| TPOX | 8 | 0.62 | 0.92 | 1.00 |
| TH01 | 9 | 0.64 | 1.35 | 1.00 |
| TH01 | 6 | 0.58 | 1.26 | 1.00 |
| vWA | 17 | 0.61 | 1.05 | 1.00 |
| vWA | 16 | 0.72 | 1.11 | 1.00 |
| D16S539 | 14 | 0.66 | 1.19 | 1.00 |
| D16S539 | 11 | 0.75 | 1.42 | 1.00 |
| D7S820 | 13 | 0.54 | 1.15 | 1.00 |
| D7S820 | 12 | 0.42 | 1.11 | 1.00 |
| D13S317 | 12 | 1.45 | 1.78 | 1.00 |
| D13S317 | 8 | 1.17 | 1.86 | 1.00 |
| D5S818 | 12 | 1.06 | 1.51 | 1.00 |

Example 6

Varying Age of Blood When DNA Purified

In this example, the quality of DNA isolated with the procedure of the invention, when blood was stored for a time period between 0 and 131 days, is compared. Over time, as the blood is stored, the DNA is known by those in the art to degrade to varying degrees. Human blood was collected in EDTA-coated vacutainer tubes and stored at 4° C. At 0, 22, 29, and 131 days after the blood was collected, the DNA from 10 µl of blood was purified by the procedure using nonporous MagneSil™ silica magnetic particles as detailed in Example 1. One microliter of each purified DNA solution was amplified (each sample analyzed in triplicate) using the Promega GenePrint® PowerPlex 1.1 system as described in Example 2. The amplified DNA was run on a denaturing polyacrylamide gel and peak heights were determined with an FMBIO® scanner and normalized to the values of day 0, as described in Example 2. Table 7 below lists the average normalized peak heights obtained and the standard deviation.

TABLE 7

| Days after blood drawn | Normalized Ave. Peak Height | Std. Deviation |
|---|---|---|
| 0 | 1.00 | 0 |
| 22 | 0.97 | 0.1 |
| 29 | 0.98 | 0.08 |
| 131 | 0.98 | 0.24 |

The normalized average peak height has minimal variation for all samples, indicating that DNA suitable for this quantitative purification procedure was obtained from blood stored for up to four months. The day 131 sample has essentially the same average peak heights, but the small alleles are somewhat higher than average and the large alleles are lower than average. This is indicated by the larger standard deviation observed when using samples prepared 131 days after the blood was drawn and stored. However, all the samples were easily genotyped and the peak heights were within acceptable ranges.

Interestingly, Example 6 shows that the size of the DNA did not significantly affect the binding and elution quantities. Thus, reliable results may be obtained without adjusting the initial calibration model based on the sample's age where older samples tend to degrade and, thus, provide smaller sizes of DNA.

Example 7

Use of Genomic DNA Isolated With MagneSil™ Silica Magnetic Particles Directly in STR Analysis This example was designed to determine if DNA needed to be eluted from the MagneSil™ silica magnetic particles in order to be used for STR Analysis.

Figure 2:
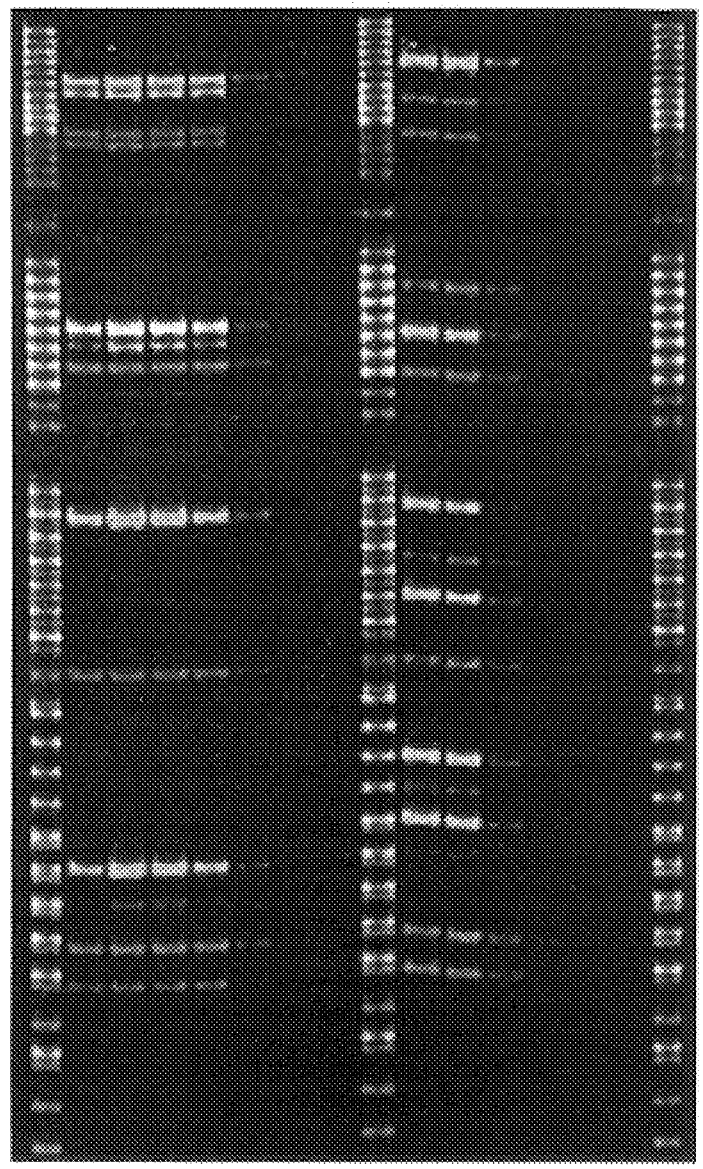
FIG. 2 is a copy of a laser-printed image produced by fluorescent detection of amplified STR loci of human genomic DNA and of DNA isolated from K562 tissue culture cells after fractionation by denaturing polyacrylamide gel electrophoresis, after amplifying the STR loci in the presence of varying amounts of MagneSil™ silica magnetic, as described in Example 7.

Six 685 ng aliquots of human genomic DNA K562 (Promega Corp.) were placed in 50 µl GTC lysis buffer (6 M Guanidine Thiocyanate, 10 mM EDTA, 10 mM Tris pH 6.0, 1% CHAPS, 1% Triton X-100) in 1.5 ml conical tubes. In a parallel experiment, 50 µl aliquots of human whole blood were placed in 1.5 ml conical tubes with 100 µl GTC lysis buffer. Decreasing amounts of silica magnetic particles (2.5, 0.5, 0.1, 0.02, 0.004, 0.0008 µg) were added to each series. The samples were processed as follows. Into a 1.5 ml conical tube was placed 400 µl GTC lysis buffer, 50 µl porous MagneSil™ silica magnetic particles (100 mg/ml) and 200 µl whole blood. The tube was vortexed for about 15 seconds. The tube was then incubated at room temperature for 10 minutes and briefly vortexed after 5 minutes. The particles were captured by placing the tube on a magnetic stand. The supernatant, separated from the particles was then removed and 650 µl wash buffer was added (25% isopropanol, 25% ethanol, 100 mM NaCl, 10 mM Tris, pH 8.0) and the tube briefly vortexed. This was repeated twice more for a total of three washes. Then, the last wash was removed and the particles were resuspended in 20 µl wash buffer. One microliter of each isolation was removed and placed in the bottom of an amplification tube and air dried for 10 minutes. These samples were then used for STR analysis and were compared to 1 ng of K562 in STR analysis using the GenePrint® PowerPlex™ 1.1 System as described in the manufacturer's instructions and in Example 2. The resulting gel is shown in FIG. 2. Lanes labeled "L" correspond to the allelic ladder.

TABLE 8

| Sample | Amount of particles in STR reaction (µg) | Lane on gel |
|---|---|---|
| K562 DNA (1 ng) | 0 (positive control) | 1 |
| K562 DNA | 2.5 | 2 |
| K562 DNA | 0.5 | 3 |
| K562 DNA | 0.1 | 4 |
| K562 DNA | 0.02 | 5 |
| K562 DNA | 0.004 | 6 |
| K562 DNA | 0.0008 | 7 |
| Blood | 2.5 | 8 |
| Blood | 0.5 | 9 |
| Blood | 0.1 | 10 |
| Blood | 0.2 | 11 |
| Blood | 0.004 | 12 |
| Blood | 0.0008 | 13 |

Comparison between the samples isolated with decreasing amounts of MagneSil™ particles and the 1 ng sample of K561 DNA indicate that extremely small amounts of genomic DNA were isolated; that the DNA bound to the particles was able to be used directly in STR reactions; and that the amount of particles required to capture DNA approximately equivalent to 1 ng K562 DNA as determined by the intensity of bands in the above described STR assay is about 0.1 µg for K562 DNA and about 0.5 µg for whole blood.

Example 8

Sequencing DNA that was Isolated by Capture on Porous and Nonporous Silica Magnetic Particles This example demonstrates that by limiting the amount of porous and nonporous silica-coated magnetic particles added to a prepared bacterial lysate containing more DNA than the maximum DNA binding capacity of the particles, DNA quantity was reliably isolated that was suitable for use in automated sequencing. This procedure eliminated the need for determining the concentration and quality of DNA by spectrophotometric analysis or other quantitative analysis that may be biased by the presence of contaminants in the DNA preparation.

DH5α bacterial cells (Life Technologies, Inc., Gaithersburg, Md.), transformed with pGEM3Zf(+) plasmid (Promega Corp., Madison, Wis.), were grown overnight, 1 ml in each well of a Beckman 2 ml BioBlock (140504). The cell density was about 2–3 OD at 600 nm. The theoretical quantity of plasmid present could range from 300–700 copies/cell and result in a yield of 1.8–4.1 μg/ml culture (Sambrook, et al., 1989, Molecular Cloning: A Laboratory Manual, $2^{nd}$ edition, Cold Spring Harbor Laboratory, Cold Spring, N.Y.). The cells were pelleted in the BioBlock by centrifugation at 2000×g for 10 minutes. The media was decanted and the plate gently tapped on a paper towel to blot off any remaining liquid.

Then, 75 μl Cell Resuspension Buffer (Promega, A711T) was added to the cell pellet and the pellet resuspended by pipetting up and down. 75 μl Cell Lysis Buffer (Promega, A712T) was added and the solution mixed by pipetting up and down four times. 100 μl Wizard™ Plus SV Neutralization Solution (Promega, A713T) was added and the solution mixed by pipetting up and down 4 times.

The tubes in the BioBlock were centrifuged at 2000×g for 10 minutes. The lysate was removed from each tube and placed in the appropriate well of a 96 well plate.

Before use, the MagneSil™ silica-coated magnetic particles (porous and nonporous) were resuspended by shaking. Then varying amounts, as listed in Table 9 below, of each type of the diluted particles were added to separate wells and gently mixed and incubated at room temperature for 10 minutes. The plate was placed on a magnet and the solution allowed to clear (about 10 seconds). The lysate was removed from each well and discarded, being careful to remove as little of the particles as possible. The plate was removed from the magnet and 40 μl 80% ethanol was added to each well.

The particles were resuspended by pipetting up and down. The plate was again placed on a magnet and the cleared lysate removed. The wash was repeated. After removing the second wash, the plate was allowed to sit for 10 minutes on the magnet. If any liquid had drained to the bottom of the wells after this time, it was removed with a pipetter. Then 10 μl nanopure water was added to each well and mixed by pipetting up and down. The plate was placed on the magnet to clear and the supernatant transferred to a clean plate.

The entirety of the samples were then sequenced, without further processing, using forward and reverse plasmid-specific primers (Promega Corp., Madison, Wis.) as listed below on an ABI 377 machine using Big-Dye™ Chemistry according to manufacturer's instructions (ABI). All of the samples could be sequenced out to 800 bases, although with varying degrees of signal intensity and accuracy. The accuracy is listed in Table 9 below, and the signal intensity is listed in Table 10 below.

Forward 5'GTTTTCCCAGTCACGAC 3' (SEQ ID No:1)
Reverse 5'CAGGAAACAGCTATGAC 3' (SEQ ID No:2)

TABLE 9

| Amount of particles (ng) in sample preparation | Accuracy (%) | | | |
|---|---|---|---|---|
| | 500 bases | 600 bases | 700 bases | 800 bases |
| 1000 (porous) | 100 | 100 | 100 | 98 |
| 500 " | 100 | 100 | 99 | 97 |
| 250 " | 100 | 100 | 99 | 98 |
| 125 " | 100 | 99 | 97 | 99 |
| 63 " | 100 | 100 | 98 | 96 |
| 1000 (nonporous) | 100 | 100 | 99 | 97 |
| 500 " | 100 | 100 | 98 | 95 |
| 250 " | 99 | 99 | 96 | 93 |
| 125 " | 75 | 0 | 0 | 0 |
| 63 " | 97 | 94 | 90 | 0 |

TABLE 10

| Sample | Amount of particles (ng) in sample preparation | Relative Signal Strength |
|---|---|---|
| 1 | 1000 (porous) | 100 |
| 2 | 500 | 53 |
| 3 | 250 | 43 |
| 4 | 125 | 65 |
| 5 | 63 | 27 |
| 6 | 1000 (nonporous) | 39 |
| 7 | 500 | 36 |
| 8 | 250 | 18 |
| 9 | 125 | 8 |
| 10 | 63 | 15 |

The results illustrate the need to determine a calibration model using various amounts of particles when using a new plasmid type, particle type, or sample type for the first time. Evident by the results in Table 9 above is that the nonporous particles have a lower binding capacity than an equivalent amount of the porous particles. This will ensure that adequate amounts of DNA are presented to the DNA sequencing reaction after the simultaneous isolation/quantitation step. In all subsequent reactions using this type of plasmid, calibration would no longer be necessary as it would be known what amount of particles is capable of being purified by the defined amount of particles under the conditions used.

Example 9

Comparison of Blood Sample on FTA® Paper Used According to Manufacturer's Protocol vs Used With Cell Lysis Buffer and Silica Magnetic Particle Separation Protocol FTA® paper (Life Technologies, Inc., Gaithersburg, Md.) is a convenient way to store blood stains. However, it presents some technical difficulties when analyzing the DNA that is on the FTA® paper. Because of the high binding capacity of the FTA® paper, and the inability to easily separate the DNA from the filter by previously known methods, very small punches of the paper must be used to avoid gross excess of DNA in amplification reactions. In addition, the capacity of the FTAO paper is for a given volume of liquid. Thus, blood with low or high white blood cell count or samples that are loaded with an excess volume of blood will give inconsistent results. The purification process recommended by the manufacturer requires five wash steps taking 20 to 30 minutes plus an additional 20 minute drying procedure at 60° C. before using the filter directly in an amplification reaction. This procedure must be repeated each time that the DNA is amplified.

In this example, a comparison is made between DNA isolation from FTA® paper using the protocol recommended by the manufacturer of the paper and DNA isolation from FTA® paper using nonporous MagneSil™ silica magnetic particles. A 113 mm² human blood stain on FTA® paper, equivalent to 100 µl of blood, was purified according to the manufacturer's protocol. A one millimeter punch was made and the punch was separated in half (equivalent to 0.5 mm² or 0.4 µl of blood). The punch was amplified using Gene-Print® PowerPlex™ 1.1 System according to the manufacturer's protocol (Promega Corp, #DC6090) and run on a denaturing polyacrylamide gel as described in Example 2.

Alternatively, a 57mm² FTA® bloodstain was heated at 95° C. for 30 minutes in 200 µl Lysis Buffer and the solution and paper were then placed in a spin basket and centrifuged for two minutes to separate the solution from the paper. Then 7 µl water containing 700 µg nonporous MagneSil™ silica magnetic particles was added and the solution incubated for 5 minutes at room temperature. The particles were then separated from the supernatant by placing the tube on a magnetic stand. The supernatant was removed and discarded. The particles were washed three times with Wash Buffer as described in Example 1 and then air dried for 5 minutes at room temperature. Then 100 µl water was added and the sample incubated at 60° C. for five minutes. The particles were separated on a magnetic stand and the solution, which contained the DNA, was collected and transferred to a clean tube. One microliter (equivalent to about 0.6 mm² FTA® punch or about 0.5 µl of blood) was amplified using the GenePrint® PowerPlex™ 1.1 DNA System and run on denaturing polyacrylamide gels as described in Example 2.

The scans of the amplification products observed on the acrylamide gel were analyzed and the peak heights each divided by the average peak height to obtain normalized values. The peak heights of the two alleles at each locus were averaged. The results are listed below in Table 11. The results show that FTA® samples, used according to the manufacturer's protocol, gave unbalanced peaks in the STR amplification reaction. The large alleles were under-amplified and the smaller alleles were overamplified. Removing the DNA from the FTA® filter paper using the silica magnetic particles as described above, provided the correct amount of DNA for use in the STR amplification reactions and no preferential amplification of different size alleles was observed.

TABLE 11

| | Normalized Peak Heights | |
|---|---|---|
| Locus | FTA Purification | Silica magnetic Purification |
| CSF1PO | 0.59 | 0.90 |
| TPOX | 0.95 | 1.11 |
| TH01 | 1.01 | 1.10 |
| vWA | 1.45 | 0.89 |

Example 10

Porous Silica Magnetic Particles and Whole Blood: Limiting Volume of Particles With Increasing Sample Size.

In this example, a constant amount (7 µl) of porous silica magnetic particles at a concentration of 100 mg/ml was used in the protocol described below to isolate DNA from triplicate 100, 200, and 300 µl samples of human whole blood. The eluted DNA was measured by UV spectrophotometry, agarose gel electrophoresis, and PicoGreen assay (Molecular Probes, Eugene, Oreg.).

Seven microliters of well-mixed porous silica magnetic particles (100 mg/ml) was pipetted into nine 2 ml screw-cap conical tubes. Then triplicate samples of 100 µl, 200 µl and 300 µl of human whole blood were each added to three of the tubes. The tubes were vortexed for 20 seconds, then incubated at room temperature for 10 minutes, mixing by vortexing once during this time. The samples were mixed again and placed on a magnetic rack. The magnetic particles were allowed to separate from the supernatant for 5 minutes at room temperature. The supernatant was then removed and discarded. Then, 400 µl of a salt wash solution was added and the tube's contents mixed by vortexing. The supernatant was separated from the particles by placing the tube on the magnetic stand and the supernatant was removed and discarded. The wash was repeated twice for a total of three washes.

Then, 400 µl of alcohol wash was added and the contents of the tube mixed by vortexing. The tube was placed on the magnetic stand and the supernatant was removed and discarded. The alcohol wash was repeated twice for a total of three washes. After removal of the final supernatant, the tube was left open to air dry at room temperature for 10 minutes. The particles were then combined with 50 µl TE (10 mM Tris, 1 mM EDTA pH 7.3). The tube was mixed and placed overnight at 5° C. The particles were separated from the supernatant on a magnetic stand and the supernatant containing the eluted DNA was transferred to a clean tube. The particles were again combined with 50 µl TE, mixed, and placed at 65° C. for 10 minutes. The particles were separated from the supernatant on a magnetic stand and the supernatant were pooled for a combined DNA eluant volume of 100 µl.

The DNA concentration in the solution was then measured by UV spectrophotometer by combining 70 µl of the solution with 280 µl TE and the absorbance at 260 nm and 280 nm was measured on a UV spectrophotometer that had been blanked with TE. The results are listed in Table 12 below.

TABLE 12

| Sample | Blood | OD260:280 | Concentration µg/ml | Yield in µg | Lane on Gel |
|---|---|---|---|---|---|
| 1 | 100 µl | 1.55 | 0.020 | 2.0 | 6 |
| 2 | " | 1.54 | 0.033 | 3.3 | 7 |
| 3 | " | 1.65 | 0.030 | 3.0 | 8 |
| 4 | 200 µl | 1.63 | 0.037 | 3.7 | 9 |
| 5 | " | 1.50 | 0.028 | 2.8 | 10 |
| 6 | " | 1.49 | 0.038 | 3.8 | 11 |
| 7 | 300 µl | 1.53 | 0.032 | 3.2 | 12 |
| 8 | " | 1.57 | 0.031 | 3.1 | 13 |
| 9 | " | 1.58 | 0.040 | 4.0 | 14 |

Figure 3:
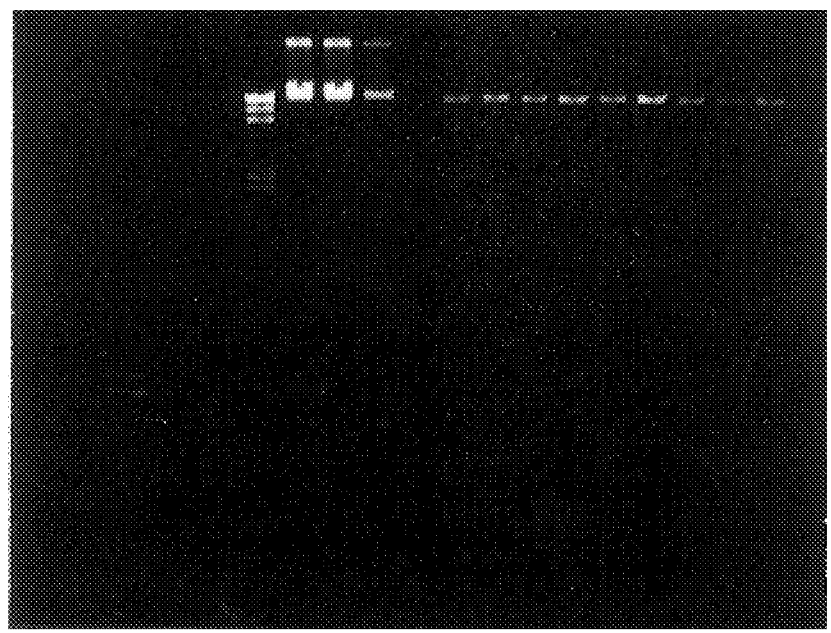
FIG. 3 shows a photograph of genomic DNA samples fractionated by gel electrophoresis and stained with ethidium bromide, wherein the samples of genomic DNA were isolated from human whole blood, using porous MagneSil™ silica magnetic particles, as described in Example 10.

Then 10 µl of each sample was run on a 1% agarose gel along with Promega G304A genomic DNA standard (lanes 2–4 in quantities of 200, 100 and 50 ng, respectively) and lambda Hind III markers G 171A (lane 1). The gel was stained with ethidium bromide and sample lanes visually compared under UV light to standards. The resulting gel is shown in FIG. 3. Sample 1 appeared to contain 150 ng total yield, sample 6 appeared to contain 800 ng total yield, and the remaining samples about 250 ng total yield. This indicated that the UV spectrophotometry data is falsely elevated by a factor of about four to ten. This may be due to residual alcohol or protein contamination as may be indicated by the low OD260:280 ratios.

A PicoGreen assay was performed according to the manufacturer's directions. The results are listed below in Table 15. From the gel photo and the PicoGreen data, the 9 samples ranged from about 250 ng to 959 ng total yield. Sample 6 appears to be an outlier point, probably resulting from uneven rehydration of the DNA in this sample.

TABLE 13

| Samples 10 µl | Raw # | Corr # | Conc | Yield (ng) |
|---|---|---|---|---|
| #1 | 94 | 57 | 1.25 | 250.8 |
| #2 | 120 | 83 | 1.83 | 365.2 |
| #3 | 107 | 70 | 1.54 | 308 |
| #4 | 153 | 116 | 2.55 | 510.4 |
| #5 | 117 | 80 | 1.76 | 352 |
| #6 | 255 | 218 | 4.80 | (959.2) |
| #7 | 117 | 80 | 1.76 | 352 |
| #8 | 100 | 63 | 1.39 | 277.2 |
| #9 | 126 | 89 | 1.96 | 391.6 |

Using the PicoGreen Quantitation data, the average yield was 418 ng. The lowest point was 250.8 ng or 60% of the average. The highest point was 959 ng (#6—probably outlier point) or 229% of the mean. If this point is disregarded in the calculation of the mean, the mean is 350 ng, the lowest point is 250 ng or 71% of the mean and the highest point is 510 ng or 145% of the mean.

This invention has been described, in detail, with particular reference to certain preferred embodiments as set forth above. It is to be understood that variations and modifications can be effected within the spirit and scope of the invention as it is set forth in the following claims.

What is claimed is:

1. A method for isolating a defined quantity of a DNA target material from other material in a medium by:
    a. providing a medium including the DNA target material;
    b. providing a discrete quantity of porous silica magnetic particles capable of reversibly binding a definable quantity of the DNA target material, the particles having an average particle diameter of about 5.0 to 8.5 microns, a nitrogen BET surface area of about 18 to 55 microns gm and an acid leach resistance of less than about 7 ppm $Fe_2O_3$, the amount of DNA target material provided in step (a) being in excess of the binding capacity of the particles;
    c. forming a complex of the silica magnetic particles and the DNA target material by combining the silica magnetic particles and the medium;
    d. removing the complex with the DNA target material from the medium by application of an external magnetic field; and
    e. separating the DNA target material of step (c) from the complex by eluting the DNA target material, whereby a defined quantity of the DNA target material is obtained.

2. The method of claim 1, wherein the silica magnetic particles are siliceous-oxide coated magnetic particles.

3. The method of claim 1 wherein the medium includes a chaotropic salt.

4. The method of claim 3 wherein the chaotropic salt comprises guanidine thiocyanate.

5. The method of claim 1, wherein the DNA target material provided in step (a) is the product of a polymerase chain reaction.

6. The method of claim 1 wherein the DNA target material is genomic DNA.

7. The method of claim 1 wherein the DNA target material is plasmid DNA.

8. The method of claim 6 further comprising analyzing the eluted genomic DNA in a DNA typing process.

9. The method of claim 1 wherein the medium is a solid support containing the DNA target material and wherein the

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Forward
      primer specific to pGEM3Zf(+) plasmid.

<400> SEQUENCE: 1
gttttcccag tcacgac                                                    17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Reverse
      primer specific to pGEM3Zf(+) plasmid.

<400> SEQUENCE: 2
caggaaacag ctatgac                                                    17

DNA target material is isolated from the solid support prior to step (c) by combining the solid support with a mixture comprising a chaotropic salt.

10. The method of claim 9 wherein the solid support is a paper.

11. The method of claim 9 wherein the mixture is heated to a temperature of from about 60° to about 100° C.

12. The method of claim 1 further comprising sequencing at least a portion of the eluted DNA target material.

13. The method of claim 1 further comprising a step of washing the complex after removal from the medium, before eluting the DNA target material from the complex.

14. The method of claims 13, wherein the complex is washed using a wash solution comprising an alcohol and a salt.

15. The method of claim 1, wherein the DNA target material eluted in step (e) is eluted with water.

16. A method of isolating a defined quantity of a DNA target material from other materials in a medium comprising the steps of:
   a. providing a medium containing the DNA target material;
   b. providing a discrete quantity of porous silica magnetic particles with the capacity to reversibly bind a definable quantity of the DNA target material per milligram of particle, the particles having an average particle diameter of about 5.0 to 8.5 microns, a nitrogen BET surface area of about 18 to 55 microns gm and an acid leach resistance of less than about 7 ppm $Fe_2O_3$, the amount of DNA target material provided in step (a) being in excess of the binding capacity of the particles;
   c. forming a mixture comprising the medium, the silica magnetic particles, and a chaotropic salt, wherein the chaotropic salt concentration in the mixture is sufficient to cause the DNA target material to adhere to the particles;
   d. incubating the mixture until at least some of the DNA target material is adhered to the silica magnetic particles;
   e. removing the silica magnetic particles and the adhered DNA target material from the mixture using an external magnetic force; and
   f. eluting the DNA target material of step (e) from the silica magnetic particles by exposing the particles to an elution solution, whereby a defined quantity of the DNA target material is obtained.

17. The method of claim 16 wherein the DNA target material is genomic DNA.

18. The method of claim 16 wherein the DNA target material is plasmid DNA.

19. The method of claim 16 further comprising sequencing at least a portion of the eluted DNA target material.

20. The method of claim 16, wherein the chaotropic salt comprises guanidine thiocyanate.

21. The method of 16, wherein the concentration of chaotropic salt in the mixture formed in step (c) is between about 0.1 M and 7 M.

22. The method of claim 16, further comprising a step of washing the silica magnetic particles after removal from the medium, before eluting the DNA target material from the particles.

23. The method of claim 22, wherein the particles are washed using a wash solution comprising an alcohol and a salt.

24. The method of claim 16 wherein the elution solution is water.

25. A method of determining a calibration model for quantitating a DNA target material in a sample type of interest, the method comprising:
   a. providing a first medium, wherein the first medium includes a first quantity of the sample type of interest;
   b. providing a second medium, wherein the second medium includes a second quantity of the sample type of interest, wherein the second quantity is greater than the first quantity of the sample type of interest;
   c. mixing a first discrete quantity of silica magnetic particles with the first medium, wherein the silica magnetic particles are capable of reversibly binding a first defined quantity of the DNA target material, thereby forming a first complex of the silica magnetic particles and the DNA target material from the first medium, the discrete quantity of the sample type of interest in the first medium containing DNA target material in excess of the binding capacity of the particles mixed with the first medium;
   d. mixing a second discrete quantity of silica magnetic particles with the second medium, wherein the silica magnetic particles are capable of reversibly binding a second defined quantity of the DNA target material, thereby forming a second complex of the silica magnetic particles and the DNA target material from the second medium, the discrete quantity of the sample type of interest in the second medium containing DNA target material in excess of the binding capacity of the particles mixed with the second medium;
   e. removing the first complex from the first medium and the second complex from the second medium by application of an external magnetic field;
   f. separately eluting the DNA target material from the first complex and second complex, producing a first eluent of isolated DNA target material from the first complex and a second eluent of isolated DNA target material from the second complex;
   g. determining the amount of DNA target material in the first and in the second eluent; and
   h. repeating steps a–g with at least one additional discrete quantity of silica magnetic particles until the amount of DNA target material isolated from two different media is determined to be about the same, thereby identifying conditions wherein the DNA binding capacity of the silica magnetic particles is exceeded.

26. The method of claim 25 wherein the first discrete quantity of particles provided in step, (c) the second discrete quantity of particles provided in step (d) and the at least one additional discrete quantity of particles provided in step (h) are the same quantity of particles.

27. A method of isolating DNA target material from a solid support, the method comprising: contacting the solid support containing the DNA target material with a chaotropic salt solution at a temperature of about 60° C. to about 100° C. thereby isolating at least a portion of the DNA target material from the solid support; isolating a defined quantity of DNA target material by adding a discrete quantity of silica magnetic particles to the isolated DNA target material to form a complex, the amount of DNA target material isolated from the solid support being in excess of the binding capacity of the particles; removing the complex with the DNA target material from the solution by application of an external magnetic field; and separating the DNA target material from the complex by eluting the DNA target material, whereby a defined quantity of the DNA target material is obtained.

28. The method of claim 27 wherein the solid support is paper.

29. The method of claim 27 wherein the chaotropic salt solution comprises a chaotropic salt and a pH buffer.

* * * * *